(12) United States Patent
Allain et al.

(10) Patent No.: US 8,664,400 B2
(45) Date of Patent: Mar. 4, 2014

(54) TRIPHENYLAMINE DERIVATIVES USEFUL AS FLUOROPHORES IN BIOLOGY, IN PARTICULAR FOR TWO-PHOTON MICROSCOPY

(75) Inventors: Clémence Allain, Antony (FR); Fabrice Charra, Marcoussis (FR); Céline Fiorini-Debuisschert, Orsay (FR); Rémy Lartia, Voiron (FR); Marie-Paule Teulade-Fichou, Paris (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 12/514,040

(22) PCT Filed: Nov. 9, 2007

(86) PCT No.: PCT/EP2007/062106
§ 371 (c)(1),
(2), (4) Date: Aug. 14, 2009

(87) PCT Pub. No.: WO2008/055969
PCT Pub. Date: May 15, 2008

(65) Prior Publication Data
US 2009/0314990 A1    Dec. 24, 2009

(30) Foreign Application Priority Data
Nov. 10, 2006    (FR) ..................................... 06 54837

(51) Int. Cl.
*C07D 213/04*    (2006.01)
*C07D 401/14*    (2006.01)

(52) U.S. Cl.
USPC .............................. 546/256; 546/264; 257/40

(58) Field of Classification Search
USPC .......................... 546/329, 256, 264; 564/307
See application file for complete search history.

(56) References Cited

U.S. PATENT DOCUMENTS 6,979,575 B1    12/2005  Romanov et al.

FOREIGN PATENT DOCUMENTS

| GB | 613458 A1 | * 11/1948 |
| GB | 622223 A1 | * 4/1949 |
| WO | 2006111726 A1 | 10/2006 |

OTHER PUBLICATIONS

STN_12514040-1_preliminary_09272010.*
Allain et al., ChemBioChem, (2007), vol. 8, p. 424-433.*
Yan et al., Journal of Molecular Structure, 2005, 733(1-3), p. 83-87.*
Cumpston et al, Nature, (1999), vol. 398, p. 51-54.*
International Search Report, PCT/EP2007/062106, dated Apr. 17, 2008.
Preliminary Examination Report, FR 0654837, dated Oct. 17, 2007.
Cai, Guolin et al., "CD Exciton Chirality Method. New Red-Shifted Chromophores for Hydroxyl Groups", J. Am. Chem. Soc. 115, 7192-7198 (1993).
Chung, Sung-Jae et al., "Cooperative Enhancement of Two-Photon Absorption in Multi-branched Structures", J. Phys. Chem. B, 103, 10741-10745 (1999).
Kajigaeshi, Shoji et al., "Halogenation Using Quaternary Ammonium Polyhalides. VII. Iodination of Aromatic Amines by Use of Benzyltrimethylammonium Dichloroiodate (1-)", Bull. Chem. Soc. Jpn., 61(2), 600-602 (1988).
Kubista, Mikael et al., "The Interactions Between the Fluorescent Dye Thiazole Orange and DNA", Biopolymers 46, 39-51 (1998).
McLaughlin, Larry W. et al., "Hoechst 33258 Tethered by a Hexa(ethylene glycol) Linker to the 5'-Termini of Oligodeoxynucleotide 15-Mers: Duplex Stabilization and Fluorescence Properties", J. Org. Chem., 62(3), 523-529 (1997).
Porres, Laurent et al., "Enhanced Two-Photon Absorption with Novel Octupolar Propeller-Shaped Fluorophores Derived from Triphenylamine", Organic Letters, 6(1), 47-50 (2004).
Yan, Yunxing et al., "Synthesis, structure and two-photon absorption properties of a new multi-branched two-photon photopolymerization initiator", J. of Molecular Structure, 733, 83-87 (2005).
Yang, Wen Jun et al., "Triphenylamine Derivatives with Large Two-Photon Cross-Sections", Organic Letters 6(9), 1389-1392 (2004).
Zongren, Zhang et al., "Synthesis and Evaluation of Polyhydroxylated Near-Infrared Carbocyanine Molecular Probes", Organic Letters, 6, 2067-2070 (2004).

* cited by examiner

*Primary Examiner* — Yong Chu
(74) *Attorney, Agent, or Firm* — Nixon Peabody LLP

(57) ABSTRACT

Triphenylamine derivatives useful as fluorophores in biology, in particular for two-photon microscopy; and
compositions comprising these derivatives, to the use of these compositions and of the derivatives themselves for labelling biological molecules (or "biomolecules") such as nucleic acids, oligonucleotides, proteins, polypeptides, plasmids, and the like, for their examination in particular by two-photon microscopy, and to biomolecules labelled with the said derivatives.

21 Claims, 11 Drawing Sheets

TRIPHENYLAMINE DERIVATIVES USEFUL AS FLUOROPHORES IN BIOLOGY, IN PARTICULAR FOR TWO-PHOTON MICROSCOPY

CROSS REFERENCE TO RELATED APPLICATIONS OR PRIORITY CLAIM

This application is a national phase of International Application No. PCT/EP2007/062106, entitled "NOVEL TRIPHENYLAMINE DERIVATIVES FOR USE AS FLUOROPHORES IN BIOLOGY, IN PARTICULAR FOR TWO-PHOTON MICROSCOPY", which was filed on Nov. 9, 2007, and which claims priority of French Patent Application No. 06 54837, filed Nov. 10, 2006.

DESCRIPTION

1. Technical Field

The present invention relates to novel triphenylamine derivatives useful as fluorophores in biology, in particular for two-photon microscopy.

It also relates to compositions comprising these derivatives, to the use of these compositions and of the derivatives themselves for labelling biological molecules (or "biomolecules") such as nucleic acids, oligonucleotides, proteins, polypeptides, plasmids, and the like, for their examination in particular by two-photon microscopy, and to biomolecules labelled with the said derivatives.

The present invention finds application in all the fields using biological and medical imaging techniques such as, for example, basic research for the structural or functional study of biological systems, applied research for clinical or therapeutic purposes, or medical diagnosis and screening.

2. Prior State of the Art

Fluorescence microscopy is a tool that is commonly used by biologists because it makes it possible to detect, quantify and provide images both of the natural components of biological systems and of elements that are foreign to these systems.

It is based on the capacity of some compounds to emit specific radiation when they are excited by an incident electromagnetic radiation having a particular wavelength. Thus, the absorption of an incident photon by the compound allows it to pass from a nonexcited state to an excited state. The compound then returns to the nonexcited state either by nonradiative deexcitation, in which case there is no fluorescence, or by radiative deexcitation with emission of a fluorescent photon which may be detected.

Few compounds naturally present in living beings have intrinsic properties of fluorescence capable of being exploited for analytical purposes because the intensity of the emitted radiation is generally too weak and the coloration too unselective. That is why biologists use particular stains endowed with fluorescent properties: fluorophores or fluorochromes. This is then referred to as secondary fluorescence.

Some fluorophores have the characteristic feature of binding specifically to biomolecules: thus, for example, 4,6-diamidino-2-phenylindole (or DAPI), which fluoresces in the blue region when it is excited by ultraviolet light, binds specifically to DNA. Other fluorophores do not have this capacity and require being grafted beforehand onto a molecule specific for the one which it is sought to detect. That is the case, for example, for rhodamine and fluorescein which can be used either to detect an antigen, in which case they are grafted onto an antibody specific for this antigen, or as cell lineage markers, in which case there are grafted onto a molecule which has good stability in biological media, such as dextran.

Within the space of a few decades, fluorescence microscopy has developed considerably by virtue of the arrival of novel optical technologies including confocal laser scanning microscopy and, more recently, two-photon excitation fluorescence microscopy, also called two-photon microscopy.

Currently, two-photon microscopy is, among all the fluorescence microscopy techniques, the one which has developed the most in the field of biology. Its principle consists in simultaneously providing two photons of identical energy to a compound in order to produce excitation equivalent to that which a single high-energy photon would have caused. For the method to be efficient, it is necessary for the photons to reach the compound within a very short interval of time of about $10^{-15}$ seconds, which has been made possible by the use of laser light sources which produce ultrashort and very intense pulses.

Two-photon microscopy has many advantages. Indeed, the photobleaching and phototoxicity processes, which are often limiting in single-photon microscopy, are limited here to a maximum degree. Furthermore, the excitation photons, which are typically situated in the near infrared region (750-900 nm), are less energetic than the photons used in single-photon microscopy. The result is that the excitation radiation is less destructive for biological samples and that it penetrates more deeply into the tissues to about 0.5 mm. Finally, two-photon microscopy has a spatial resolution that is as good as that of confocal laser scanning microscopy, that is to say of the order of the micrometre.

It should be noted that the principle of a multiphoton excitation is not limited to a two-photon excitation and that three-photon microscopy experiments have already been successfully carried out.

Currently, the fluorophores used in two-photon microscopy are the same as those used in single-photon microscopy. Now, these fluorophores have poor two-photon fluorescence properties, in particular in terms of efficient absorption section, which limits the extent of the applications of two-photon microscopy in biology.

It would therefore be desirable to be able to have fluorophores that are better suited to two-photon fluorescence and, in particular, to a use of this technique for the examination of biological systems.

During the past few years, the two-photon absorption properties of triphenylamine derivatives have been the subject of a number of studies and notable results have been obtained in organic media for applications relating to the field of materials and optoelectronics.

Mention may thus be made of:

the studies by Chung et al. (J. Phys. Chem. B 1999, 103, 10741-10745 [1]) relating to three derivatives obtained by respectively functionalizing one, two or the three phenyl groups of triphenylamine with a succession of three aromatic rings including an oxadiazole ring, via a vinyl group;

those by Porres et al. (Organic Letters 2004, 6(1), 47-50 [2]) relating to a series of derivatives derived from the functionalization of the three phenyl groups of triphenylamine with a strongly electron-attracting group via an acetylene group;

those by Yang et al. (Organic Letters 2004, 6(9), 1389-1392 [3]) relating to three derivatives obtained by functionalizing the three phenyl groups of triphenylamine with one or more aromatic rings, via an ethylene group; and finally those by Yan et al. (J. of Molecular Structure 2005, 733, 83-87 [4]) relating to the spectral properties of a derivative obtained by functionalizing the three phenyl groups of triphenylamine with pyridinyl groups, via a vinyl group.

However, all these derivatives have a number of characteristics which prevent their use as markers for biological systems, in particular a large size such as will disrupt the behaviour of biomolecules, insolubility in water and the absence of functionalities that are likely to allow their grafting onto biomolecules for use in secondary fluorescence.

The inventors therefore set themselves the aim of developing fluorophores which are perfectly suited to the use of two-photon fluorescence in the field of biology.

DISCLOSURE OF THE INVENTION

This aim and others are achieved by the present invention which provides, firstly, compounds derived from triphenylamine, useful as markers either in direct fluorescence, or in secondary fluorescence and which correspond to the general formula (I) below:

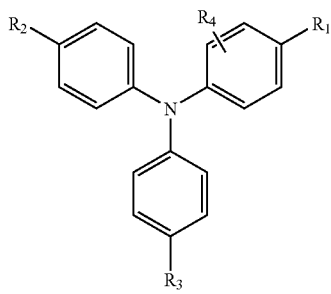

(I)

in which:
$R_4$ represents a hydrogen atom or a linking group, in which case:
1) if $R_4$ represents a hydrogen atom, then:
$R_1$ represents a linking group or a group of formula (II) below:

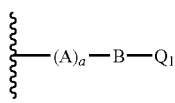

(II)

in which:
$Q_1$ represents:
a heterocyclic group of formula (i) below:

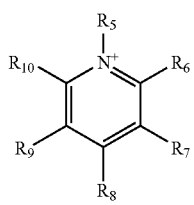

(i)

in which $R_5$ represents a hydrocarbon group; any one of $R_6$ to $R_{10}$ represents a covalent bond linking the said heterocyclic group to B, while the others from $R_6$ to $R_{10}$ represent, independently of each other, a hydrogen atom or a hydrocarbon group; or a heterocyclic group of formula (ii) or (iii) below:

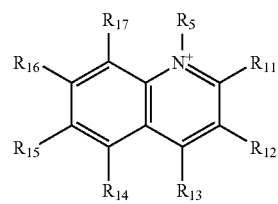

(ii)

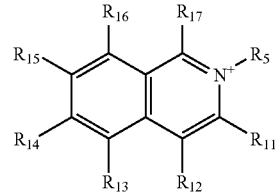

(iii)

in which $R_5$ represents a hydrocarbon group; any one of $R_{11}$ to $R_{17}$ represents a covalent bond linking the said heterocyclic group to B, while the others from $R_{11}$ to $R_{17}$ represent, independently of each other, a hydrogen atom or a hydrocarbon group, it being possible for $R_{12}$, $R_{14}$ and $R_{16}$ to also form, respectively with $R_{11}$ and/or $R_{13}$, $R_{13}$ and/or $R_{15}$, and with $R_{15}$ and/or $R_{17}$, a bridging group; or a heterocyclic group of formula (iv) below:

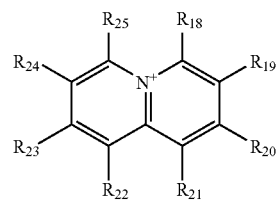

(iv)

in which any one of $R_{18}$ to $R_{25}$ represents a covalent bond linking the said heterocyclic group to B, while the others from $R_{18}$ to $R_{25}$ represent, independently of each other, a hydrogen atom or a hydrocarbon group, it being possible for $R_{19}$, $R_{21}$, $R_{23}$ and $R_{25}$ to also form, respectively with $R_{18}$ and/or $R_{20}$, $R_{20}$ and/or $R_{22}$, $R_{22}$ and/or $R_{24}$, and with $R_{24}$ and/or $R_{18}$, a bridging group; or a heterocyclic group of formula (v) below:

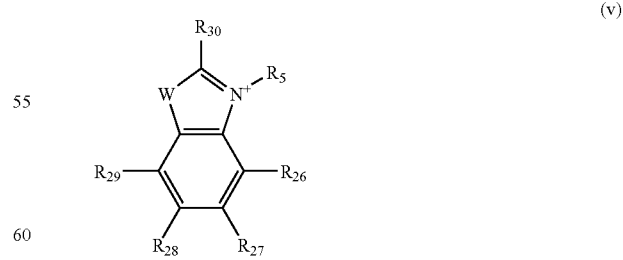

(v)

in which $R_5$ represents a hydrocarbon group; W represents an oxygen or sulphur atom or a group —$N(R_{31})$— in which $R_{31}$ is a hydrogen atom or a hydrocarbon group, or a group —$C(R_{31})(R_{32})$— in which $R_{31}$ and $R_{32}$ are, independently of each other, a hydrogen atom or a hydrocarbon group; $R_{30}$ represents a covalent bond linking the said heterocyclic group to B, while $R_{26}$ to $R_{29}$ represent, independently of each other, a hydrogen atom or a hydrocarbon group, it being possible for $R_{27}$ to also form with $R_{26}$ and/or $R_{28}$ a bridging group, it being possible for $R_{28}$ itself to form with $R_{29}$ a bridging group;

a is equal to 0 (in which case A is absent) or 1 (in which case A is present);

A and B represent the groups below:

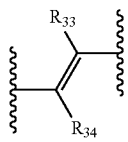
(A)

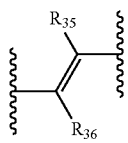
(B)

in which $R_{33}$ to $R_{36}$ represent, independently of each other, a hydrogen atom or a hydrocarbon group, it being possible for $R_{33}$ and $R_{36}$ to each also form with $R_{34}$ and/or $R_{35}$ a bridging group;

when $R_1$ represents a group of formula (II) above, then $R_2$ also represents a group of formula (II) above while, when $R_1$ represents a linking group, then $R_2$ represents a group of formula (III) below:

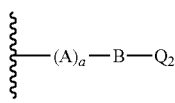
(III)

in which:

$Q_2$ represents:

a heterocyclic group corresponding to any one of the formulae (i) to (v) above; or a heterocyclic group of formula (vi) below:

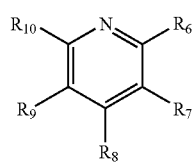
(vi)

in which $R_6$ to $R_{10}$ have the same meaning as in the formula (i) above; or a heterocyclic group of formula (vii) or (viii) below:

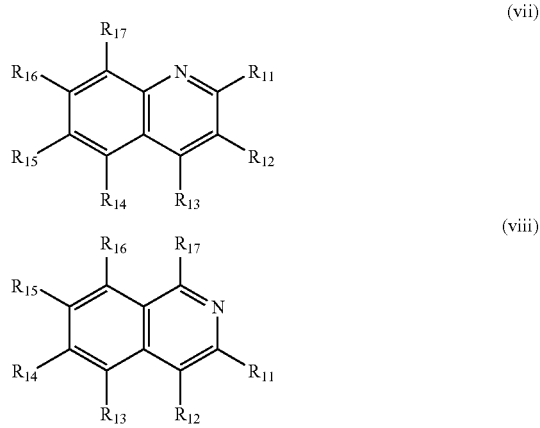

in which $R_{11}$ to $R_{17}$ have the same meaning as in the formulae (ii) and (iii) above; or a heterocyclic group of formula (ix) below:

in which W, $R_{26}$ to $R_{30}$ have the same meaning as in the formula (v) above;

a, A and B have the same meaning as above;

when $R_1$ represents a linking group, then $R_3$ represents a group of formula (III) above while, when $R_1$ represents a group of formula (II) above, then $R_3$ represents a hydrogen or halogen atom, a hydrocarbon group or a group of formula (II) above;

2) if $R_4$ represents a linking group, then $R_1$ and $R_2$ represent a group of formula (III) above while $R_3$ represents a hydrogen or halogen atom, a hydrocarbon group or a group of formula (III) above;

in which the linking group is a functional group capable of allowing the grafting, by a chemical reaction, of the compound on a biomolecule, or a hydrocarbon group comprising such a functional group, and in which each of the abovementioned hydrocarbon groups may be substituted with one or more substituents, which are identical or different, and comprise one or more heteroatoms.

The subject of the invention is also the isomers of these compounds and the addition salts of these compounds and of their isomers.

The expression "any one of $R_6$ to $R_{10}$ represents a covalent bond linking the said heterocyclic group to B" used above means that the heterocyclic group in question is directly linked to B by a covalent bond involving any one of the carbon atoms of the ring constituting it.

Likewise, the expressions "any one of $R_{11}$ to $R_{17}$ represents a covalent bond linking the said heterocyclic group to B" and "any one of $R_{18}$ to $R_{25}$ represents a covalent bond linking the said heterocyclic group to B" used above mean that the relevant heterocyclic groups are directly linked to B by a covalent bond involving any one of the carbon atoms of the rings constituting them.

In accordance with the invention, the hydrocarbon groups which may be used for $R_5$ to $R_{36}$ in the groups of formulae (II) and (III) above and for $R_3$ may be saturated, mono- or polyunsaturated, aliphatic (that is to say linear or branched), mono- or polycyclic groups.

As mentioned above, these groups may, on the one hand, be substituted with one or more substituents, which are identical to each other or different from each other, and, on the other hand, comprise one or more heteroatoms, in which case this or these heteroatoms may either form a bridge in the said hydrocarbon groups or be carried by them in the form of substituents.

In the context of the present invention, the expression "heteroatom" is understood to mean any atom other than carbon or hydrogen, such as, for example, an oxygen, nitrogen, sulphur, halogen, phosphorus, boron or silicon atom, oxygen, nitrogen, sulphur and halogen (fluorine, iodine, chlorine, bromine) atoms being preferred.

Thus, the hydrocarbon groups which may be used for $R_5$ to $R_{36}$ and for $R_3$ may be in particular:

linear or branched alkyl groups, such as, for example, methyl, ethyl, n-propyl, isopropyl, butyl, isobutyl, sec-butyl, tert-butyl, pentyl, isopentyl or hexyl groups;

linear or branched alkenyl or alkynyl groups, such as, for example, ethenyl or ethynyl, propenyl or propynyl, isopropenyl or isopropynyl, butenyl or butynyl, isobutenyl or isobutynyl, sec-butenyl or sec-butynyl, tert-butenyl or tert-butynyl, pentenyl or pentynyl, isopentenyl or isopentynyl groups;

cycloalkyl groups such as, for example, cyclopentyl or cyclohexyl groups;

cycloalkenyl or cycloalkynyl groups such as, for example, cyclopentenyl or cyclopentynyl groups, a cyclohexenyl or cyclohexynyl group;

aromatic groups containing one or more fused rings such as, for example, cyclopentadienyl, phenyl, naphthyl, pyrenyl or anthracenyl groups;

heteroaromatic groups containing one or more fused rings such as, for example, furanyl, pyrrolyl, thiophenyl, oxazolyl, pyrazolyl, thiazolyl, imidazolyl, triazolyl, pyridinyl, pyranyl, quinolinyl, isoquinolinyl, pyrazinyl or pyrimidinyl groups; or alternatively groups derived from the abovementioned groups by one or more substitutions, this or these substitutions preferably corresponding to halogen atoms or to aliphatic groups comprising at least one heteroatom such as, for example, a group —COOR", —CHO, —OR", —SR", —SCOR", —SO$_2$R", —NR"R'", —CONR"R'", —C(Hal)$_3$, —OC(Hal)$_3$, —C(O)Hal or —CN in which R" and R'" represent a hydrogen atom or an alkyl group, while Hal represents a halogen atom, preferably a fluorine, chlorine or bromine atom.

To avoid the compounds suffering from steric hindrance, it is preferable that the hydrocarbon groups which may be used for $R_5$ to $R_{36}$ do not contain more than 10 carbon atoms (substituent(s) inclusive) and are, if possible, $C_1$ to $C_6$ groups and, better still, $C_1$ to $C_4$ groups, in the case of aliphatic groups, or groups with a single 5- or 6-membered ring in the case of cyclic groups.

In a particularly preferred manner, the hydrocarbon groups which may be used for $R_5$ to $R_{36}$ are $C_1$ to $C_4$ alkyl groups, in particular methyl or ethyl.

In accordance with the invention, the bridging groups which are capable of being formed by:

$R_{12}$, $R_{14}$ and $R_{16}$, respectively with $R_{11}$ and/or $R_{13}$, $R_{13}$ and/or $R_{15}$, and with $R_{15}$ and/or $R_{17}$, in the groups of formulae (ii), (iii), (vii) and (viii);

$R_{19}$, $R_{21}$, $R_{23}$ and $R_{25}$ forming also possibly, respectively with $R_{18}$ and/or $R_{20}$, $R_{20}$ and/or $R_{22}$, $R_{22}$ and/or $R_{24}$, and with $R_{24}$ and/or $R_{18}$, in the groups of formula (iv);

$R_{27}$ with $R_{26}$ and/or $R_{28}$ and by $R_{28}$ with $R_{29}$ in the groups of formulae (v) and (ix); and by $R_{33}$ and $R_{36}$ with $R_{34}$ and/or $R_{35}$ in the groups A and B;

are divalent groups formed by the succession of n atoms chosen from carbon, nitrogen, oxygen and/or sulphur atoms and in which n is advantageously chosen so that the formation of these bridging groups results in the formation of 5- or 6-membered rings or heterocycles.

Thus:

the bridging groups which are capable of being formed by $R_{13}$ with $R_{14}$ in the groups of formulae (ii) and (vii), by $R_{12}$ with $R_{13}$ and by $R_{16}$ with $R_{17}$ in the groups of formulae (iii) and (viii), by $R_{18}$ with $R_{25}$ and by $R_{21}$ with $R_{22}$ in the group of formula (iv), by $R_{33}$ and $R_{36}$ with $R_{34}$ and/or $R_{35}$ in the groups A and B are, preferably, groups formed by the succession of 2 or 3 atoms; while all the other bridging groups which are capable of being formed in the groups of formulae (ii) to (ix) are preferably groups formed by the succession of 3 or 4 atoms.

Moreover, these bridging groups are preferably unsaturated groups whose unsaturations typically correspond to double bonds. Preferably, these double bonds form, with each other and/or with the other double bonds present in the compounds, a system of conjugated double bonds.

Moreover, the bridging groups may be substituted with one or more substituents, which are identical or different, as long as the succession of atoms forming them comprises one or more carbon and/or nitrogen atoms. This or these substituents preferably correspond to halogen atoms, to aliphatic groups comprising at least one heteroatom such as, for example, —COOR", —CHO, —OR", —SR", —SCOR", —SO$_2$R", —NR"R'", —CONR"R'", —C(Hal)$_3$, —OC(Hal)$_3$, —C(O)Hal or —CN groups in which R", R'" and Hal have the same meaning as above, or alternatively to neutral groups such as alkyl, for example methyl or ethyl, groups.

For use in direct fluorescence, the compounds according to the invention typically correspond to the general formula (I) in which $R_4$ represents a hydrogen atom, $R_1$ represents a group of formula (II) as defined above, $R_2$ represents a group of formula (II) identical to $R_1$, while $R_3$ represents a hydrogen or halogen atom, a hydrocarbon group as defined above or alternatively a group of formula (II) identical to $R_1$ and $R_2$.

Such compounds comprise at least two positively charged nitrogen atoms whose charges are counterbalanced by anions. These anions may be in particular halide ions such as I$^-$, Cl$^-$, Br$^-$, F$^-$, nitrate ions, phosphate ions such as PO$_4^{3-}$ or PF$_6^-$, carbonate ions, carboxylate ions such as CH$_3$COO$^-$, sulphite ions such as SO$_3^{2-}$ or HSO$_3^-$, sulphate ions such as SO$_4^{2-}$ or HSO$^{4-}$, sulphonate ions such as CF$_3$SO$_3^-$ or alkyl-SO$_3^-$, or alternatively BF$_4^-$ ions.

For these compounds to have good solubility in water, the group of formula (II) constituting $R_1$ and $R_2$, and optionally $R_3$, is preferably a group in which a is equal to 0, which means that A is absent, while $R_{35}$ and $R_{36}$ of B represent hydrogen atoms or $C_1$ to $C_4$ alkyl groups, advantageously methyl or ethyl groups.

Although, in this group of formula (II), $Q_1$ can represent any one of the heterocyclic groups of formulae (i) to (v) above, it is preferable however that it represents either a group of formula (i) as defined above, or a group of formula (v) as defined above.

Groups of formula (II) corresponding to these criteria are typically:

(a) groups of formula (II-1) below:

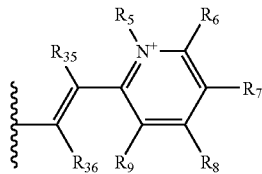

(II-1)

in which $R_5$ represents a $C_1$ to $C_4$ alkyl, preferably methyl or ethyl, group, while $R_6$ to $R_9$, $R_{35}$ and $R_{36}$ represent, independently of each other, a hydrogen atom or a $C_1$ to $C_4$ alkyl, preferably methyl or ethyl, group;

(b) groups of formula (II-2) below:

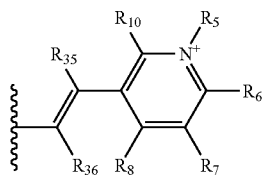

(II-2)

in which $R_5$ represents a $C_1$ to $C_4$ alkyl, preferably methyl or ethyl, group, while $R_6$ to $R_8$, $R_{10}$, $R_{35}$ and $R_{36}$ represent, independently of each other, a hydrogen atom or a $C_1$ to $C_4$ alkyl, preferably methyl or ethyl, group;

(c) groups of formula (II-3) below:

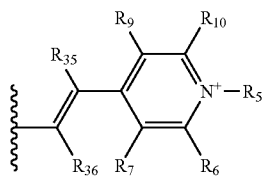

(II-3)

in which $R_5$ represents a $C_1$ to $C_4$ alkyl, preferably methyl or ethyl, group, while $R_6$, $R_7$, $R_9$, $R_{10}$, $R_{35}$ and $R_{36}$ represent, independently of each other, a hydrogen atom or a $C_1$ to $C_4$ alkyl, preferably methyl or ethyl, group; and (d) groups of formula (II-4) below:

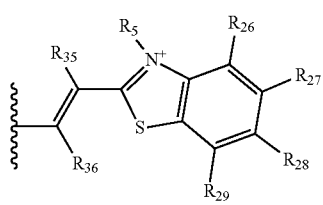

(II-4)

in which $R_5$ represents a $C_1$ to $C_4$ alkyl, preferably methyl or ethyl, group, while $R_{26}$ to $R_{29}$, $R_{35}$ and $R_{36}$ represent, independently of each other, a hydrogen atom or a $C_1$ to $C_4$ alkyl, preferably methyl or ethyl, group.

In the context of their studies, the inventors observed that the compounds of general formula (I) in which at least $R_1$ and $R_2$ represent a group of formula (II-5) below:

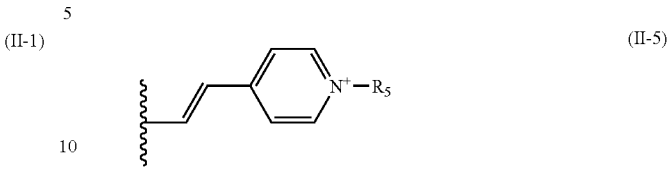

(II-5)

in which $R_5$ represents a $C_1$ to $C_4$ alkyl, preferably methyl or ethyl, group, and which corresponds to the formula (II-3) above in which $R_6=R_7=R_9=R_{10}=R_{35}=R_{36}=H$, exhibit a range of properties rarely possessed by the fluorophores conventionally used in biology, namely:

a good solubility in water and, therefore, in biological media;

an excellent resistance to the effects of light radiation (no photobleaching or photodegradation);

fluorescence in the red region which, on the one hand, does not risk interfering with the signals emitted in the green region by the cellular components which fluoresce naturally and, on the other hand, is less harmful to the cells than fluorescence in the blue and green regions;

a large efficient two-photon absorption section; and especially, a particularly high affinity for DNA under conditions similar to physiological conditions, manifested by a large increase in their fluorescence in the presence of this biomolecule and conferring on these compounds a most particular advantage for the labelling of DNA.

Accordingly, these compounds are particularly preferred for use in direct fluorescence.

Particularly concerned are those in which $R_1$ and $R_2$ are both a group of formula (II-5) in which $R_5$ represents a methyl group, while $R_3$ represents a hydrogen atom or a group of formula (II-5) identical to $R_1$ and $R_2$.

By way of examples of such compounds, there may be mentioned bis[4-(2-N-methylpyridinium-4-ylvinyl)phenyl]phenylamine and tris[4-(2-N-methyl-pyridinium-4-ylvinyl)phenyl]amine halides and, in particular, iodides.

For a secondary fluorescence, the compounds according to the invention correspond typically to the general formula (I) in which:

either $R_4$ represents a hydrogen atom, in which case $R_1$ represents a linking group, $R_2$ represents a group of formula (III) as defined above and $R_3$ represents a group of formula (III) identical to $R_2$;

or $R_4$ represents a linking group, in which case $R_1$ represents a group of formula (III) as defined above, $R_2$ represents a group of formula (III) identical to $R_1$, while $R_3$ represents a hydrogen or halogen atom, a hydrocarbon group as defined above or alternatively a group of formula (III) identical to $R_1$ and $R_2$.

The inventors having observed that the nature of the linking group has very little or no influence on the fluorescent properties of the compounds according to the invention, the linking group or the functional group which the linking group contains when the latter is a hydrocarbon group may be chosen from a large number of functional groups, as long as they are capable of chemically reacting with a functional group belonging to the biomolecule(s) which it is intended to label with these compounds.

An exhaustive list of linking groups which are capable of being used cannot therefore be given, but persons skilled in the art will perfectly well know how to choose an appropriate linking group.

Thus, for example, they will know that, in order to promote the water solubility of the compounds, the linking group should be particularly a very hydrophilic group such as a polyalcohol, a polyol, a polyethylene glycol or a polyamine.

They will also know that in order to graft the compounds on a nucleic acid, a linking group of the polyethylene glycol type will be particularly suitable as described by Mac Laughin et al. (J. Org. Chem. 1997, 62(3), 523-529 [5]).

Likewise, they will know that the use of a polyol such as a saccharide (galactose for example), apart from increasing the solubility, also minimizes aggregation in an aqueous medium (Zongren et al., Org. Lett. 2004, 6, 2067-2070 [6]).

They will further know that, in order to graft the compounds on a protein or a polypeptide and, in particular, on an antibody or an antigen, via a functional group of an amino acid, it will be possible to use a linking group consisting of or containing a carboxylic acid group, a group derived from a carboxylic acid (for example, an acid halide or an acid anhydride), an activated ester (for example, an N-hydroxysuccinimidyl, pentafluorophenyl or para-nitro-phenyl ester), a primary amine group or a leaving group of the halide, tosylate, mesylate or maleimide type, and the like.

In accordance with the invention, when $R_4$ represents the linking group, then it is preferably at the α position of the group $R_1$.

Moreover, when, in the group of formula (III) constituting $R_2$ and $R_3$ when $R_4$ is a hydrogen atom, or $R_1$, $R_2$, and optionally $R_3$, when $R_4$ is a spacer group, $Q_2$ is a heterocyclic group corresponding to any one of the formulae (i) to (v), then the compounds contain at least two positively charged nitrogen atoms whose charges are, here again, counterbalanced by anions such as those mentioned above.

The group of formula (III) constituting $R_2$ and $R_3$ when $R_4$ is a hydrogen atom, or $R_1$, $R_2$, and optionally $R_3$, when $R_4$ is a spacer group, is preferably a group in which a is equal to 0, while $R_{35}$ and $R_{36}$ of B represent hydrogen atoms or $C_1$ to $C_4$ alkyl, advantageously methyl or ethyl, groups.

Moreover, in this group of formula (III), $Q_2$ preferably represents either a group of formula (vi) as defined above, or a group of formula (ix) as defined above.

Groups of formula (III) satisfying these criteria are typically:

(a) groups of formula (III-1) below:

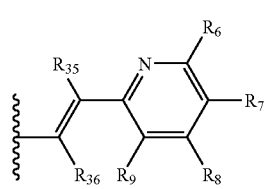

(III-1)

in which $R_6$ to $R_9$, $R_{35}$ and $R_{36}$ represent, independently of each other, a hydrogen atom or a $C_1$ to $C_4$ alkyl, preferably methyl or ethyl, group;

(b) groups of formula (III-2) below:

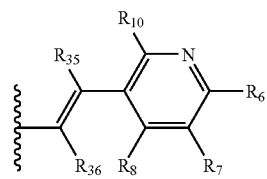

(III-2)

in which $R_6$ to $R_8$, $R_{10}$, $R_{35}$ and $R_{36}$ represent, independently of each other, a hydrogen atom or a $C_1$ to $C_4$ alkyl, preferably methyl or ethyl, group;

(c) groups of formula (III-3) below:

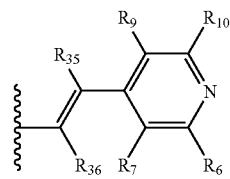

(III-3)

in which $R_6$, $R_7$, $R_9$, $R_{10}$, $R_{35}$ and $R_{36}$ represent, independently of each other, a hydrogen atom or a $C_1$ to $C_4$ alkyl, preferably methyl or ethyl, group; and (d) groups of formula (III-4) below:

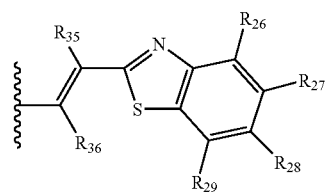

(III-4)

in which $R_{26}$ to $R_{29}$, $R_{35}$ and $R_{36}$ represent, independently of each other, a hydrogen atom or a $C_1$ to $C_4$ alkyl, preferably methyl or ethyl, group.

For use in secondary fluorescence, preference is given more particularly to the compounds of general formula (I) in which $R_4$ is a linking group, while $R_1$, $R_2$ and $R_3$ all represent:

either a group of formula (III-5) below:

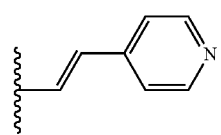

(III-5)

(which corresponds to a group of formula (III-3) above in which $R_6=R_7=R_9=R_{10}=R_{35}=R_{36}=H$);

or a group of formula (III-6) below:

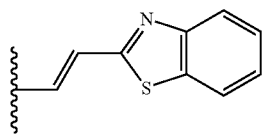

(III-6)

(which corresponds to a group of formula (III-4) above in which $R_{26}=R_{27}=R_{28}=R_{29}=R_{35}=R_{36}=H$).

Examples of such compounds are in particular:

ethyl 4-{5-[bis(4-[(E)-2-(1,3-benzothiazol-2-yl)vinyl]phenyl)amino]-2-[(E)-2-(1,3-benzothiazol-2-yl)vinyl] phenoxy}butanoate;

4-{5-[bis(4-[(E)-2-(1,3-benzothiazol-2-yl)vinyl]phenyl) amino]-2-[(E)-2-(1,3-benzothiazol-2-yl)vinyl] phenoxy}butanoic acid;

succinimidyl 4-{5-[bis(4-[(E)-2-(1,3-benzothiazol-2-yl)vinyl]phenyl)amino]-2-[(E)-2-(1,3-benzothiazol-2-yl)vinyl]phenoxy}butanoate;

(3-(8-bromooctyloxy)-{4-[(E)-2-(benzothiazol-2-yl)vinyl]}-N,N-bis-{4-[(E)-2-(benzothiazol-2-yl)vinyl] phenyl}aniline;

(3-(8-(2,5-dioxo-1-aza)cyclopent-3-enyl)octyloxy)-{4-[(E)-2-(benzothiazol-2-yl)vinyl]}-N,N-bis-{4-[(E)-2-(benzothiazol-2-yl)vinyl]phenyl}aniline;

(3-(9-bromononyloxy)-4-{4-[(E)-2-(pyridin-4-yl)vinyl]phenyl}-N,N-bis-{4-[(E)-2-(pyridin-4-yl)vinyl] phenyl}aniline;

3-(9-bromononyloxy)-4,4',4''-tris(2-((E)-pyridin-4-yl)vinyl) triphenylamine tris-methiodide;

methyl 4-(N,N-bis(4-(2-(pyridin-4-yl)vinyl))phenyl)aminobenzoate; and methyl 4-(N,N-bis-(4-(2-(benzothiazol-2-yl)vinyl))phenyl) aminobenzoate.

The compounds according to the invention may be prepared by synthesis routes that are within the capability of persons skilled in the art since many methods which make it possible to derivatize triphenylamine have indeed been described in the literature such as, for example, in the above-mentioned references [1] to [4].

The starting compound is generally a triphenylamine that is mono-, di- or trisubstituted with a halogen atom, for example a bromine or iodine atom, or an aldehyde which is subjected to one or more successive coupling reactions in order to graft, on the phenyl rings, the groups respectively constituting $R_1$, $R_2$, $R_3$ and/or $R_4$ in the compounds of general formula (I).

These coupling reactions such as, for example, the Heck or Wittig-Hörner reaction which makes it possible to graft vinyl compounds on phenyl rings, are reactions that are commonly used in organic synthesis.

The coupling may sometimes lead to products containing one or more substituents which can be separated by purification. The use of silica gel chromatography is then recommended.

According to the objective of the user, it is possible to proceed in several steps. If $R_1$ to $R_3$ are identical, then, starting with a starting compound containing for example —Br, —I or —CHO functional groups, it is sufficient to cause the reaction of a compound containing a functional group of the alkene, phosphonate or phosphonium type in at least stoichiometric proportions. In the case where $R_3$ is different from $R_1$ and $R_2$, or in the case where $R_1$ is different from $R_2$ and $R_3$, it is possible to carry out the procedure in the same manner provided that $R_3$ in the first case or $R_1$ in the second case does not react during the coupling. Of course, it is also possible to resort to the use of protecting groups to protect one or more functional groups capable of reacting in order to orient the coupling reactions and to favour these reactions in a particular direction.

The subject of the invention is also a composition which comprises at least one compound corresponding to the general formula (I) as defined above, in solution in a solvent.

Its subject is also the use of at least one compound corresponding to the general formula (I) as defined above, or of a composition comprising such a compound for labelling biomolecules.

Taking into account the two-photon fluorescence properties exhibited by the compounds according to the invention, this labelling will be preferably carried out for the purpose of examining the said biomolecules by two-photon microscopy. As such, it is also possible to use the compounds according to the invention as markers for biomolecules such as proteins in other applications such as, for example, in epifluorescence microscopy or in confocal microscopy.

The subject of the invention is also a biomolecule labelled with at least one compound corresponding to general formula (I) as defined above, this biomolecule being preferably a nucleic acid or a fragment of a nucleic acid (oligonucleotide for example), a protein, a polypeptide or a fragment of a protein or of a polypeptide.

The invention will be understood more clearly in the light of the additional description which refers to exemplary embodiments of compounds according to the invention and of a demonstration of their properties.

Of course, these examples are given only by way of illustration of the invention and do not in any way constitute a limitation thereto.

DETAILED DISCLOSURE OF EXEMPLARY EMBODIMENTS

Example 1

Figure 1:
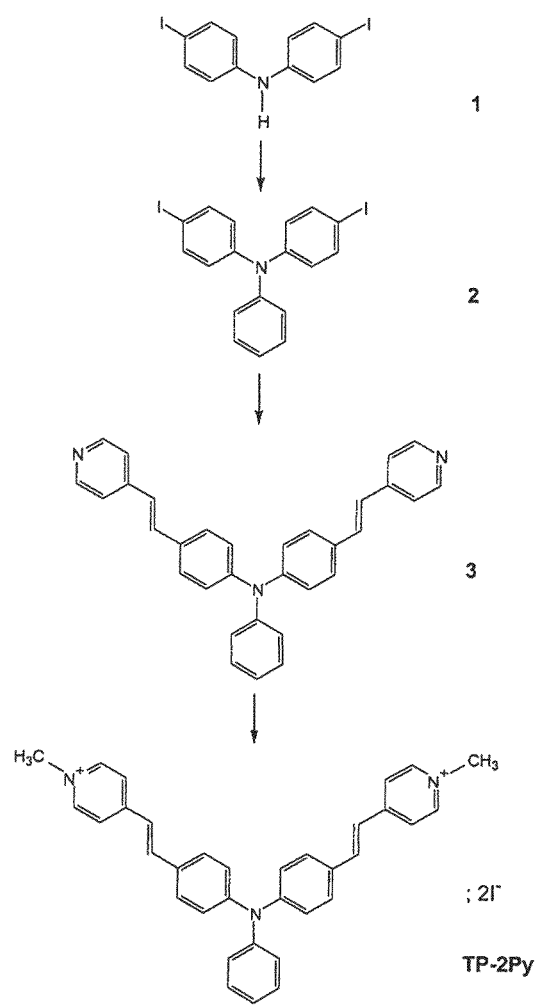
FIG. 1 illustrates the scheme for the synthesis of a first compound according to the invention (TP-2Py).

Compounds Useful in Direct Fluorescence 1.1. Bis[4-(2-N-methylpyridinium-4-ylvinyl)phenyl]phenylamine iodide The title compound or compound TP-2Py, which corresponds to the compound of general formula (I) in which $R_4=R_3=H$, $R_1=R_2=$group of formula (II-5) in which $R_5=$—$CH_3$, is synthesized starting with 4,4'-diiododiphenylamine or compound 1, according to the scheme shown in FIG. 1.

4,4'-diiodophenylamine was obtained beforehand as described by Kajigaeshi in Bull. Chem. Soc. Jpn. 1998, 61(2), 600-602 [7].

Synthesis of 4,4'-Diiodotriphenylamine or compound 2

4,4'-Diiododiphenylamine (406 mg, 1 eq.) and 2-(trimethylsilyl)benzene trifluoromethanesulphonate (244 μL, 602 mg, 1.04 eq.) are dissolved in dry acetonitrile (6 ml). After stirring for 1 minute, finely ground CsF is added (295 mg, 2.01 eq.) and the resulting suspension is stirred for 3 days protected from light. Next, the solution is evaporated, taken up in n-hexane and filtered on silica. After evaporating the mother liquors, compound 2 is isolated in the form of a fine white powder (yield: 86%).

Synthesis of 4,4'-bis(2-((E)-pyridin-4-yl)vinyl)triphenylamine or compound 3

Compound 2 (108 mg, 220 μmol), palladium acetate (6 mg, 12%) and tris(o-tolyl)phosphine (15 mg, 22%) are introduced into a dry reactor which is then purged with nitrogen. Next, 70 μL of 4-vinylpyridine (660 μmol) and 3 ml of a degassed triethylamine/dimethylformamide mixture (TEA/DMF:2/1, v/v) are successively added. The mixture is stirred at 85-90° C., under nitrogen for 3 hours. Next, its temperature is brought to room temperature and the solvents are evaporated under high vacuum. The oily residue is diluted with dichloromethane and washed with water several times. Next, the organic phase is dried and concentrated. The oily residue is purified by chromatography on silica gel (elution: dichloromethane/methanol 100/0 to 95/5, v/v). 79 mg (200 mmol) of compound 3 are thus obtained in the form of an orange powder (yield: 80%).

Synthesis of TP-2Py

Compound 3 (37 mg, 82 μmol) is dissolved in 3 mL of a iodomethane/methanol mixture (2/1, v/v) and the solution thus obtained is heated under reflux for 24 hours. Next, the crude product is concentrated, taken up in ether and filtered. The red solid obtained is washed several times with ether and with pentane to give 52 mg (71 μmol) of TP-2Py in the form of a dark red powder (yield: 87%).

$^1$H NMR (DMSO-$d_6$, 300 MHz) δ: 8.80 (d, 6.6 Hz, 4H); 8.17 (d, 6.6 Hz, 4H); 7.97 (d, 16.2 Hz, 2H); 7.70 (d, 8.7 Hz, 4H); 7.35-7.46 (m, 4H); 7.08-7.28 (m, 7H); 4.23 (s, 6H).

$^{13}$C NMR (DMSO-$d_6$, 75 MHz) δ: 153.1; 148.8; 146.2; 145.4; 140.6; 130.6; 130.2; 126.6; 125.8; 123.6; 123.5; 122.0; 47.2.

1.2. Tris[4-(2-N-methylpyridinium-4-ylvinyl)phenyl] amine iodide

Figure 2:
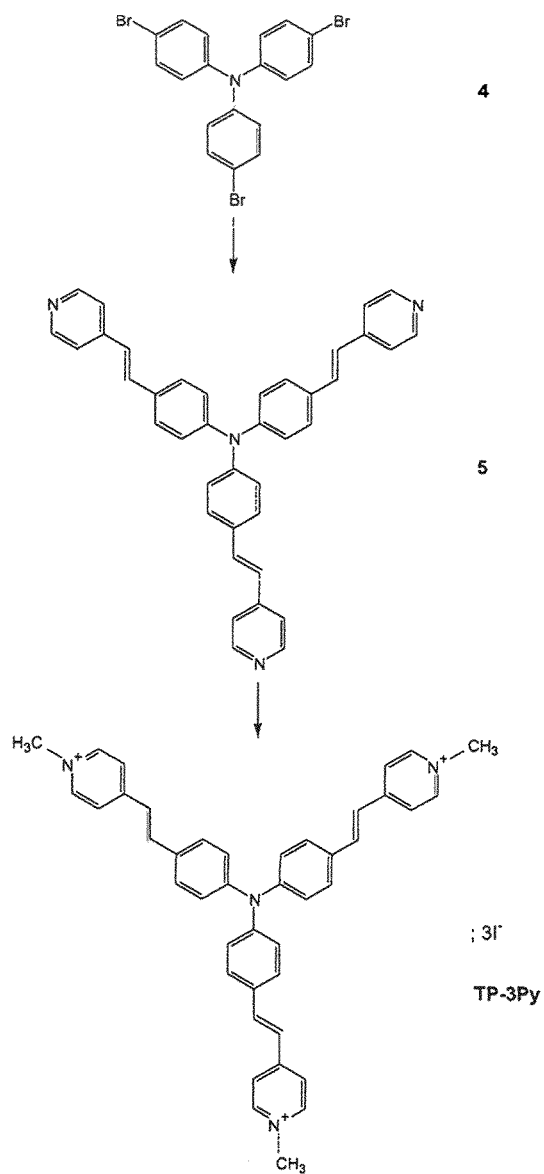
FIG. 2 illustrates the scheme for the synthesis of another compound according to the invention (TP-3Py).

The title compound or compound TP-3Py, which corresponds to the compound of general formula (I) in which $R_4$=H, $R_1$=$R_2$=$R_3$=group of formula (II-5) in which $R_5$=—$CH_3$, is synthesized starting with tris(4-bromophenyl)amine or compound 4, which is commercially available, according to the scheme shown in FIG. 2.

Synthesis of tris[4-(2-pyridin-4-ylvinyl)phenyl]amine or compound 5

Compound 4 (1 g, 2.07 mmol, 1 eq.), palladium acetate (23 mg, 0.104 mmol, 0.05 eq.) and tris-o-tolylphosphine (95 mg, 0.311 mmol, 0.15 eq.) are introduced into a dry reactor which is then purged with nitrogen. One mL of 4-vinylpyridine (0.98 g, 9.32 mmol, 4.5 eq.) and 5.4 mL of a TEA/DMF mixture (2/1, v/v) are successively added. The mixture is stirred at 85-90° C., under nitrogen for 25 hours. Next, its temperature is brought to room temperature and the solvents are removed under high vacuum. The product is diluted with 120 mL of dichloromethane, washed with 3×30 mL of a saturated sodium carbonate solution and then dried. The volume of dichloromethane is reduced and the product is precipitated by adding hexane and cooling to 4° C.

0.943 g of compound 5 is thus obtained in the form of an orange powder (yield: 85.5%).

Synthesis of TP-3Py

Iodomethane in a large excess (1.5 mL) is added to a suspension of compound 5 (64 mg, 0.115 mmol) in 1.5 mL of methanol. The mixture, which immediately becomes deep red in colour, is left stirring overnight. The product is then precipitated by adding diethyl ether and filtered.

0.103 g of TP-3Py is thus obtained in the form of a red solid (yield: 91%).

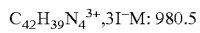 $C_{42}H_{39}N_4^{3+}, 3I^-$ M: 980.5    Empirical formula $^1$H NMR (DMF d7) δ (ppm): 4.50 (s, 9H, Me); 7.28 (d, J=8.4 Hz, 6H); 7.64 (d, J=16.2 Hz, 3H); 7.90 (d, J=8.7 Hz, 6H); 8.20 (d, J=16.2 Hz, 3H); 8.40 (d, J=6.6 Hz, 6H); 9.06 (d, J=6.6 Hz, 6H).

$^{13}$C NMR (DMF d7) δ (ppm): 47.0; 122.3; 123.7; 124.6; 130.1; 131.3; 140.5; 145.3; 148.3; 153.4

MS (ESI+): 363.11 ($[C_{42}H_{39}N_4I]^{2+}/2$, 10%); 199.75 ($[C_{42}H_{39}N_4]^{3+}/3$, 100%).

Example 2

Properties of TP-2Py and TP-3Py

2.1. Solubility in Water

TP-2Py and TP-3Py have a high solubility in water since it was possible to obtain 0.5 to 1 mM aqueous solutions of these compounds without any precipitate being formed. This aqueous solubility is a real advantage especially for biological applications since it makes it possible to work in an aqueous medium and not to use an organic solvent such as DMSO which, although conventionally used in this field, is deleterious for cellular membranes.

Furthermore, unlike the markers commonly used in biology such as derivatives of cyanines (thiazole orange for example) which form aggregates in an aqueous medium, aqueous solutions of TP-2Py and TP-3Py follow the Beer-Lambert law, at least up to a concentration of 50 μM. By way of comparison, thiazole orange exists, under the conditions in which it is conventionally used, that is to say at a concentration of 36 μM and at a temperature of 20° C., in the form of dimers (Kubista et al., Biopolymers 1998, 46, 39-51 [8]).

2.2. Emission and Single-Photon Absorption Properties

The study of the single-photon absorption properties of TP-2Py and TP-3Py demonstrated that these two compounds exhibit a high absorption in the visible domain and that their molar extinction coefficients (ε) are, in glycerol, 37 400 L/mol·cm (at 474 nm) for TP-2Py and 66 000 L/mol·cm (at 474 nm) for TP-3Py.

The maximum absorption wavelengths of these two compounds are in the 450-500 nm range and are therefore perfectly compatible with the use of the Titanium:Sapphire lasers which are used in two-photon microscopy and which are generally tunable in the 750-900 nm spectral range.

Moreover, fluorescence measurements carried out on TP-2Py and TP-3Py in solution in an aqueous medium (10 mM sodium cacodylate, pH 7.0) showed that the presence of DNA in this medium results in a strong hypochromism, of about 20%, of TP-2Py and of TP-3Py and a shift towards the red region of their absorption spectra, this shift being all the more pronounced the higher the DNA concentration of the media.

Figure 3:
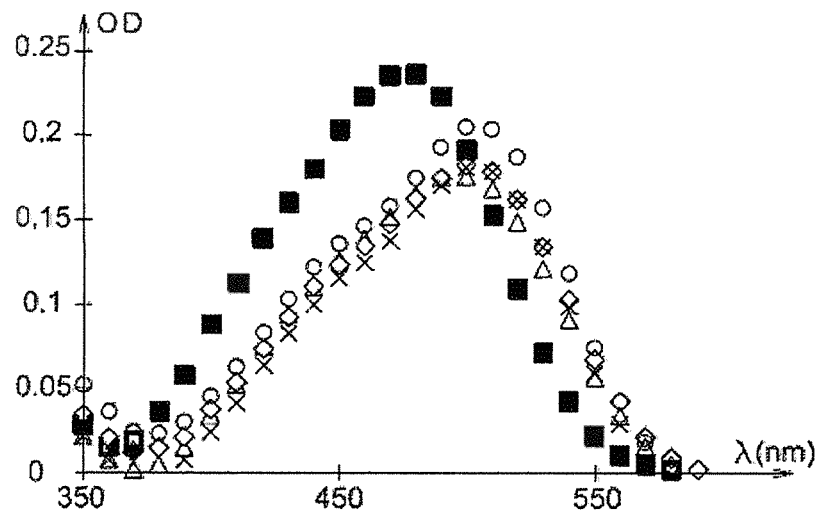
FIG. 3 illustrates the influence of the presence of DNA on the absorption spectrum (optical density (OD) as a function of the wavelength ($\lambda$)) of a compound according to the invention (TP-2Py) in solution (5 µM) in a sodium cacodylate buffer (10 mM, pH 7.0); represented in this figure are the absorption spectrum of the compound as obtained in the absence of DNA (■) and its absorption spectra as obtained in the presence of 0.5 equivalent (Δ), 1 equivalent (◊), 2 equivalents (X) and 5 equivalents (○) of DNA.
Figure 4:
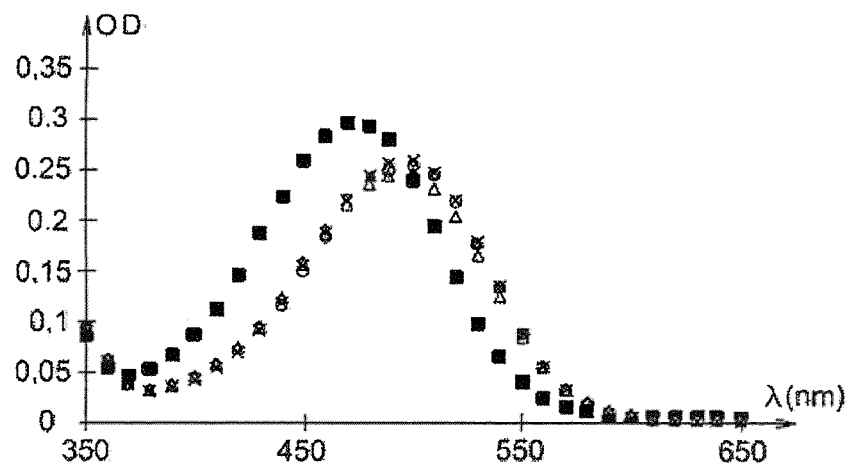
FIG. 4, which is a figure similar to FIG. 3, illustrates the influence of the presence of DNA on the absorption spectrum (optical density (OD) as a function of the wavelength ($\lambda$)), of another compound according to the invention (TP-3Py), also in solution (5 µM) in a sodium cacodylate buffer (10 mM, pH 7.0); here again, represented in this figure are the absorption spectrum of the compound as obtained in the absence of DNA (■) and its absorption spectra as obtained in the presence of 0.5 equivalent (Δ), 1 equivalent (◊), 2 equivalents (X) and 5 equivalents (○) of DNA.

These results, which are illustrated in FIGS. 3 and 4, which represent the absorption spectra of TP-2Py and TP-3Py, respectively, obtained from 5 μM solutions of these compounds, before and after a duplex DNA of 26 base pairs of self-complementary sequence (hereinafter "ds26") has been added to them, in amounts ranging from 0.5 to 5 equivalents, show a high affinity of TP-2Py and TP-3Py for DNA under conditions similar to physiological conditions.

The presence of DNA in an aqueous medium containing TP-2Py and TP-3Py also proved to have the effect of greatly increasing the fluorescence properties of these compounds at their maximum emission of fluorescence, that is to say around 660-680 nm.

Figure 5:
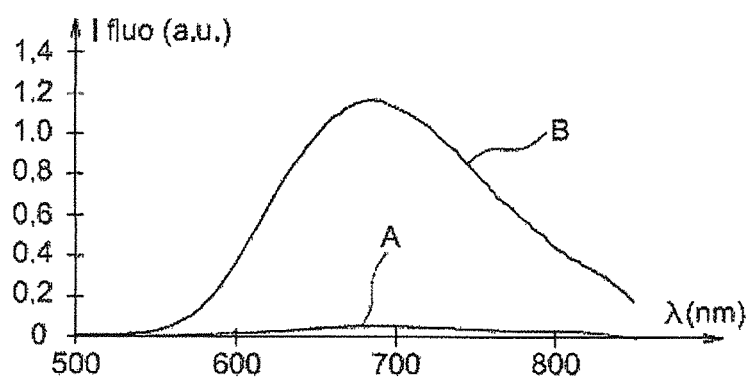
FIG. 5 illustrates the influence of the presence of DNA on the emission spectrum (fluorescence intensity ($I_{fluo}$) expressed as counts per second (cps), as a function of the wavelength $\lambda$), of a compound according to the invention (TP-3Py) in solution (3 µM) in a sodium cacodylate buffer (10 mM, pH 7.0) and for an excitation at 474 nm; represented in this figure are the emission spectrum of the compound in the absence of DNA (curve A) and that obtained in the presence of 1 equivalent of DNA (curve B).
Figure 6:
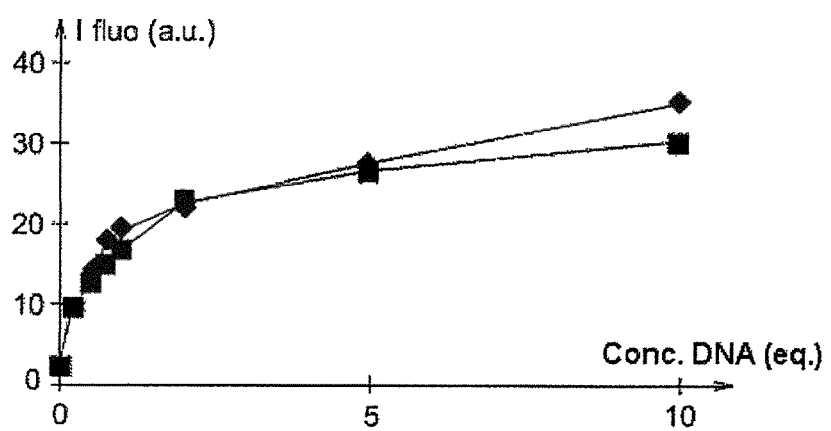
FIG. 6 illustrates the influence of the presence of DNA on the intensity of the fluorescence emitted by two compounds according to the invention (TP-2Py (■) and TP-3Py (♦)) in solution (1 μM) in a sodium cacodylate buffer (10 mM, pH 7.0) and respectively for an excitation at 474 nm and 478 nm; represented in this figure are the variations in the fluorescence intensity ($I_{fluo}$) expressed in arbitrary units, as a function of the number of DNA equivalents.

This exaltation effect is illustrated in FIG. 5 which represents the emission spectra obtained from a 3 μM solution of TP-3Py, before and after 1 equivalent of ds26 has been added to it, for an excitation at 474 nm, and in FIG. 6 which represents the variations in fluorescence intensity ($I_{fluo}$) obtained from 3 μM solutions of TP-1Py (▲), TP-2Py (■) and TP-3Py (♦), also for excitation at 474 nm, as a function of the number of equivalents of ds26 added.

The latter figure shows that the intensity of fluorescence emitted by these compounds can increase up to 20 times according to the number of equivalents of DNA.

Similar fluorescence studies, but carried out in glycerol, have shown an even more pronounced exaltation of the fluorescence properties of TP-2Py and TP-3Py, of the order of 100 times.

It should be noted that such an affinity for DNA is rare in the markers conventionally used in biology, which confers a great advantage on compounds such as TP-2Py and TP-3Py, this affinity ensuring a priori a high level of molecular luminescence in a cellular context.

The affinity of TP-2Py and TP-3Py for DNA was determined by fluorometric titration under stringent conditions (10 mM sodium cacodylate buffer, pH 7.0 supplemented with 100 mM NaCl) and using ds26 as DNA. For the two compounds, a dissociation constant $K_d$ of the order of the micromolar was obtained, confirming their very high affinity for DNA.

2.3. Photostability

The capacity of TP-3Py to withstand the effects of irradiation was tested and compared to that of a fluorophore conventionally used as DNA marker in epifluorescence and confocal microscopies, namely TO-PRO-3 (1-(N,N,N-trimethylaminopropyl)-4-{2-[3-methyl-2,3-dihydro-(benzo-1,3-thiazole)-2-ethylidene]vinyl}quinolinium iodide).

Figure 7:
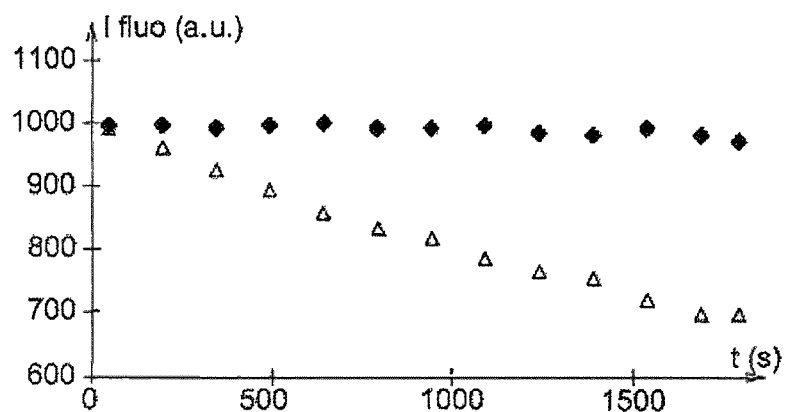
FIG. 7 represents the variations in the fluorescence intensity ($I_{fluo}$) expressed in arbitrary units, as a function of time, expressed in seconds, as measured for a compound according to the invention (TP-3Py (♦)) and for TO-PRO-3 (Δ), during irradiation with a 150 W xenon-mercury lamp.

As illustrated by FIG. 7, which represents the variations in the fluorescence intensity ($I_{fluo}$) expressed in arbitrary units, as a function of time, expressed in seconds, as measured for TP-3Py and TO-PRO-3 during an irradiation with a 150 W xenon-mercury lamp for about thirty minutes, the fluorescence emission of TP-3Py is scarcely modified by the irradiation, whereas that of TO-PRO-3 decreases by more than 40%.

2.4. Two-Photon Absorption Properties

The two-photon absorption properties of the compounds according to the invention were assessed using the two-photon-induced fluorescence (TPIF) technique and by means of a Titanium:Sapphire femtosecond laser source with pulses of 90 fs to 76 MHz which can be tuned to 750-840 nm.

The relative TPIF intensities of the compounds according to the invention were measured relative to a conventional reference marker, fluorescein, and a compound that is structurally very close to TP-2Py and TP-3Py, tris[4-(2-pyridin-4-ylvinyl)phenyl]amine.

In a first instance, the measurements were carried out using TP-2Py and TP-3Py in glycerol, the fluorescein and the tris[4-(2-pyridin-4-ylvinyl)phenyl]amine being, for their part, respectively in water (pH>10) and in dichloromethane.

Figure 8:
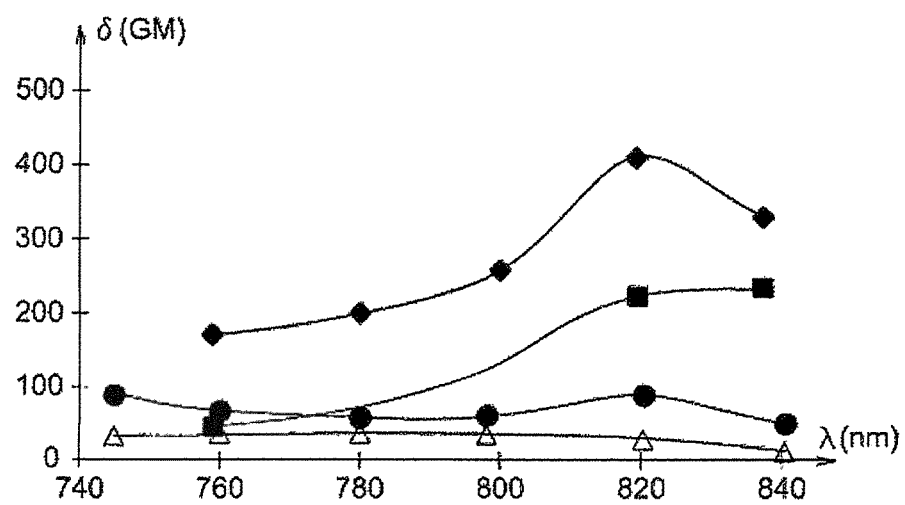
FIG. 8 represents the variations in the efficient section for two-photon absorption δ, expressed as Goppert-Mayer, as a function of the wavelength (nm) as measured for two compounds according to the invention (TP-2Py (■) and TP-3Py (♦)), for a compound which is structurally very close to them, tris[4-(2-pyridin-4-ylvinyl)phenyl]amine (●), and for fluorescein (Δ), fluorescein being in solution in water (pH>10), TP-2Py and TP-3Py being in solution in glycerol and the tris-[4-(2-pyridin-4-ylvinyl)phenyl]amine being in solution in dichloromethane.

As shown in FIG. 8, which represents the variations in the efficient two-photon absorption section δ, expressed in Göppert-Mayer, as a function of the wavelength (nm), as obtained for TP-2Py (■), TP-3Py (♦), tris[4-(2-pyridin-4-ylvinyl)phenyl]amine (●) and fluorescein (Δ), a relative maximum is observed in the region of 820 nm for TP-2Py and TP-3Py. The absorption maximum at 2 photons is therefore at a wavelength less than twice the absorption wavelength at 1 photon (2×474 nm=950 nm), which shows that other excited states, at a higher energy participate in the two-photon absorption process.

Figure 9:
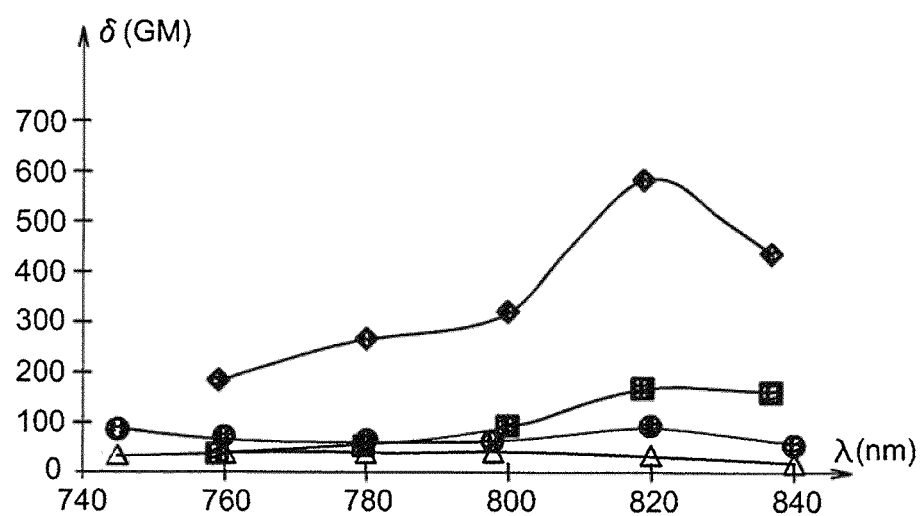
FIG. 9 represents the results of a test similar to that whose results are presented in FIG. 8, but which was carried out using the two compounds according to the invention (TP-2Py (■) and TP-3Py (♦)) in solution in a sodium cacodylate buffer (10 mM, pH 7.3) supplemented with 5 equivalents of herring testis DNA.

Next, the measurements were carried out using TP-2Py and TP-3Py in a sodium cacodylate buffer (10 mM, pH 7.3) supplemented with 5 equivalents of herring testis DNA. As shown in FIG. 9, the spectra obtained for TP-2Py and TP-3Py in the presence of DNA are identical to those previously observed in glycerol, this being for all the excitation wavelengths.

The optical properties of TP-2Py and TP-3Py are summarized in Table I below, in which ε corresponds to the molar extinction coefficient, expressed in L/mol·cm, ΦF corresponds to the quantum fluorescence yield and δ corresponds to the efficient two-photon absorption section, expressed in Göppert-Mayer (GM).

TABLE I

|  | ε (L/mol · cm) | $\lambda_{abs.}$ (nm) | $\lambda_{em.}$ (nm) | ΦF | δ (GM) |
|---|---|---|---|---|---|
| TP-2Py | 37 400 (glyc.) | 491 (glyc.) | 656 (glyc.) | 0.112 (glyc.) | 315 (glyc.) |
|  | 39 800 (Na cacodyl.) | 474 (Na cacodyl.) |  |  |  |
|  | 31 400 (DNA) | 509 (DNA) | 665 (DNA) | 0.07 (DNA) | 200 (DNA) |
| TP-3Py | 66 000 (glyc.) | 491 (glyc.) | 665 (glyc.) | 0.123 (glyc.) | 700 (glyc.) |
|  | 59 000 (Na cacodyl.) | 474 (Na cacodyl.) |  |  |  |
|  | 51 000 (DNA) | 499 (DNA) | 684 (DNA) | 0.021 (DNA) | 700 (DNA) |

It is apparent that TP-3Py has a large efficient two-photon absorption section since it reaches a value of 700 GM in glycerol and of 700 GM and in the presence of DNA. This value is very markedly greater than those obtained for DAPI (0.16 GM), for fluorescein (38 GM) and for rhodamine 6G (100 GM) which is in fact considered as one of the best fluorophores for two-photon microscopy.

It should be noted that tris[4-(2-pyridin-4-ylvinyl)phenyl]amine, which is structurally very close to TP-3Py, exhibits, like the latter, an excitation maximum at around 820 nm but the value of its efficient two-photon absorption section is only 58 GM according to the literature and 90 GM according to the measurements performed by the Inventors.

2.5. Study by Microscopy

In order to demonstrate the potential of the compounds according to the invention for imaging DNA, CHO K1 (Chinese Ovarian Hamster K1) cells were respectively treated with TP-2Py, TP-3Py, DAPI and TP-2Py/DAPI and TP-3Py/DAPI mixtures, and then examined by epifluorescence microscopy and by confocal laser microscopy.

The CHO-K1 cells, cultured beforehand in wells, on glass supports coated with polyornithine, containing a commercially available standard culture medium, were fixed using a formaldehyde (4%) solution in PBS.

The cells were then incubated, at room temperature and for 20 minutes, in the presence of the markers or mixtures of markers to be tested (in aqueous solution) and then washed with PBS buffer (13 mM NaCl, 0.27 mM KCl, 0.15 mM $KH_2PO_4$, 0.8 mM $Na_2HPO_4$, pH 7.4) in order to remove the excess marker. The concentrations of TP-2py and TP-3Py were set at 2 μM, while that of DAPI was set at 3 μM. The cells were then prepared conventionally for microscopic examination.

Epifluorescence microscopy examinations were carried out with a Nikon Eclipse E 800 microscope fitted with a 60× (1.4) lens and a Nikon DXM 1200 digital apparatus, while the confocal microscopy examinations were carried out with a Leica DM6000 microscope comprising an SP2 unit equipped with a 63× (1.4) lens and an HeNe laser for excitation of the markers.

Figure 10A:
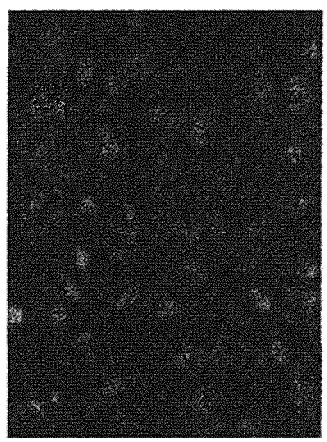
FIGS. 10A and 10B correspond to images, taken in epifluorescence microscopy, of CHO K1 cells treated with a mixture of a compound according to the invention (TP-3Py 2 μM) and of DAPI (3 μM); these images were taken at the fluorescence emission maximum of the compound according to the invention in the case of FIG. 10A and at the fluorescence emission maximum of DAPI in the case of FIG. 10B.
Figure 10B:
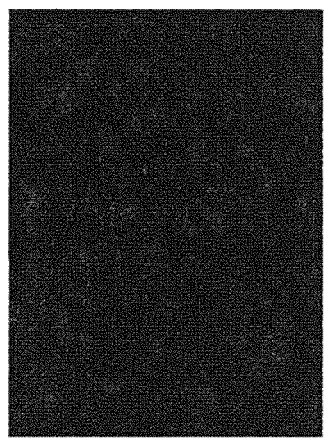
Figure 10C:
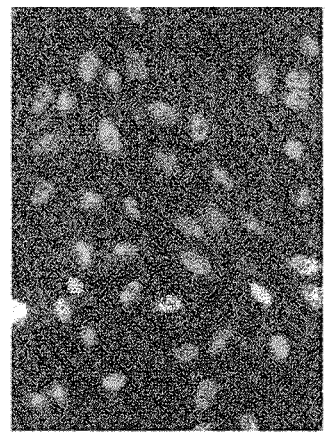
FIG. 10C corresponds to the superposition (overlapping), performed by computer processing, of FIGS. 10A and 10B which shows the colocalization of the markers in the nucleus.

As shown in FIGS. 10A, 10B and 10C, which correspond to images of cells that have been treated with a mixture of TP-3Py and DAPI, taken by epifluorescence microscopy at the maximum fluorescence emission of TP-3Py in the case of FIG. 10A, at the maximum fluorescence emission of DAPI in the case of FIG. 10B and by superposing these images by computer processing in the case of FIG. 10C, an intense fluorescence is observed (in the red region) due to the treatment with TP-3Py and this fluorescence is located exclusively in the nucleus, which once again demonstrates the remarkable affinity which this compound has for DNA. As regards the cytoplasm, a very high contrast is obtained and no background noise was detected. Moreover, considering the light intensity at the focal point of the microscope lens, it is evident from the examination that TP-3Py is very stable.

Figure 11A:
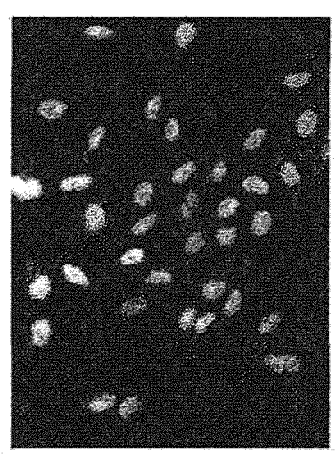
FIGS. 11A and 11B correspond to images, taken in epifluorescence microscopy, of CHO K1 cells treated with a mixture of another compound according to the invention (TP-2Py 2 μM), and of DAPI (3 μM); these images were taken at the fluorescence emission maximum of the compound according to the invention in the case of FIG. 11A and at the fluorescence emission maximum of DAPI in the case of FIG. 11B.
Figure 11B:
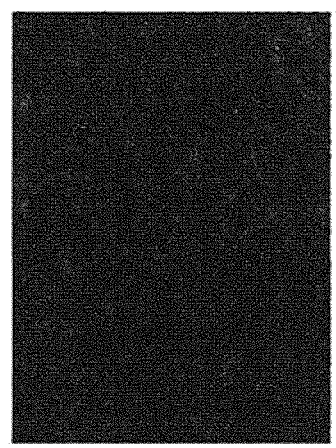
Figure 11C:
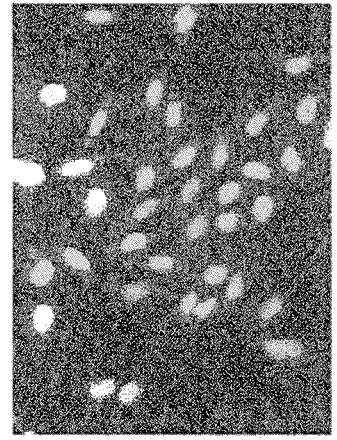
FIG. 11C corresponds to the superposition (overlapping), carried out by computer processing, of FIGS. 11A and 11B which shows the colocalization of the markers in the nucleus.
Figure 12A:
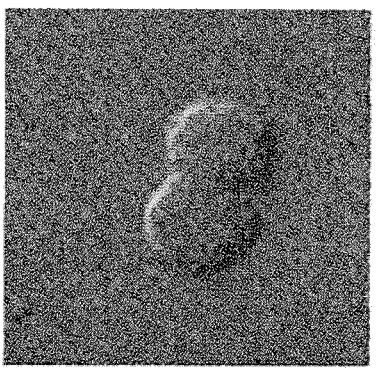
FIGS. 12A, 12B, 12C, 12D, 12E and 12F correspond to images, taken in phase contrast microscopy (FIGS. 12A and 12D) and in confocal microscopy (FIGS. 12B and 12E) and by coupling these two methods (FIGS. 12C and 12F), of CHO K1 cells which are in two different stages of mitosis, these cells having been treated beforehand with a compound according to the invention (TP-3Py 2 μM); these images were taken at the fluorescence emission maximum of the compound according to the invention.
Figure 12B:
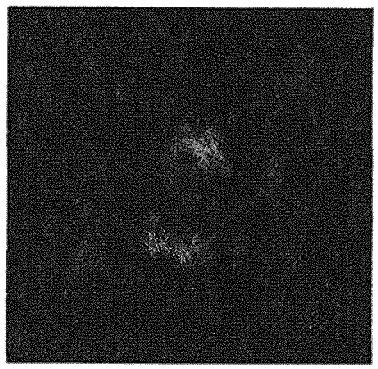
Figure 12C:
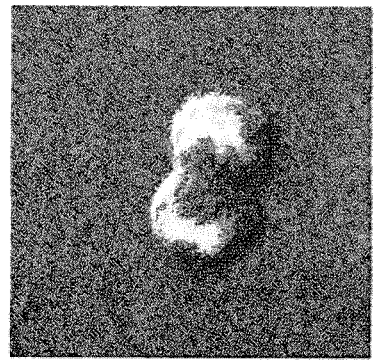
Figure 12D:
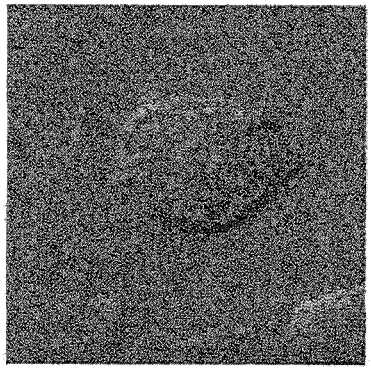
Figure 12E:
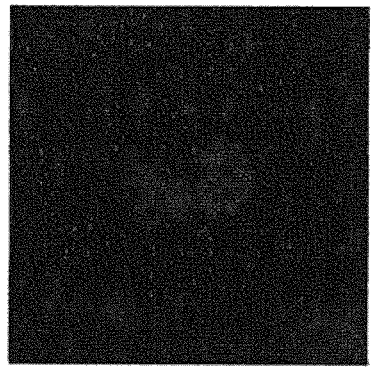
Figure 12F:
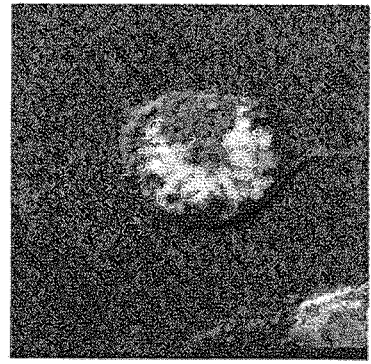

Similar results were obtained for the cells treated with a TP-2Py/DAPI mixture as shown by FIGS. 11A, 11B and 11C.

Moreover, as shown in FIGS. 12A to 12F which correspond to images of cells that have been treated with TP-3Py, taken by phase contrast microscopy (FIGS. 12A and 12D), by confocal microscopy (FIGS. 12B and 12E) and by superposing these two methods (FIGS. 12C and 12F), at the maximum fluorescence emission of TP-3Py, the latter made it possible to obtain, by coupling phase contrast and confocal microscopies, images of chromosomes in the anaphase with a very high degree of sharpness and a high resolution, with a very clear definition of the limits of the cell.

Thus, despite the fact that the quantum yields obtained in vitro for TP-2Py and TP-3Py are relatively average, it is found that by virtue of their large efficient two-photon absorption section and their low quantum yield in the free state, these compounds offer a high contrast.

These compounds emit in the red region, which is a clear advantage on the fluorophores emitting in the blue or green region because not only is the use of the latter accompanied by interferences due to the cellular components which fluoresce naturally in the green region, but what is more the blue-green light is likely to cause damage to the cells. For these reasons, a better detection may be obtained because the diffusion in the medium is more limited.

Example 3

Compounds Useful in Secondary Fluorescence 3.1. Ethyl 4-{5-[bis(4-[(E)-2-(1,3-benzothiazol-2-yl) vinyl]phenyl)amino]-2-[(E)-2-(1,3-benzothiazol-2-yl)vinyl]phenoxy}butanoate The title compound or compound 12, which corresponds to the compound of general formula (I) in which $R_4$=linking group —O(CH$_2$)$_3$C(O)OC$_2$H$_5$, $R_1$=$R_2$=$R_3$=group of formula (III-6), is synthesized from methyl 2-methoxy-4-aminobenzoate or compound 6, which is commercially available, according to the scheme shown in FIG. 13.

Synthesis of methyl 2-methoxy-4-(N,N-bis(4-methoxycarbonylphenyl)amino)benzoate or compound 7

Palladium acetate (186 mg, 828 µmol, 5%) and tris-tert-butylphosphine (7.7 mL, 2.48 mmol, 15%; 10% solution in hexane (m/m)) are introduced into 30 mL of dry and degassed toluene. After stirring for 15 minutes, methyl 4-bromobenzoate (10.7 g, 49.7 mmol, 3 eq.), compound 6 (3.0 g, 16.6 mmol, 1 eq.) and caesium carbonate (13.5 g, 41.4 mmol, 2.5 eq.) are added. The solution is heated under reflux for 17 hours, and then cooled and diluted with dichloromethane (100 mL). The solution is filtered on Celite, evaporated and purified by chromatography (elution with a gradient from n-hexane/dichloromethane 2/1, v/v, to dichloromethane) to give 6.35 g of compound 7 in the form of a light yellow powder (yield: 89%).

Synthesis of (4-{bis[4-(hydroxymethyl)phenyl] amino}-2-methoxyphenyl)methanol or compound 8

A solution of compound 7 (1.35 g, 3 mmol) in 20 mL of THF is added dropwise to a suspension of lithium aluminium hydride (LiAlH$_4$, 1.7 g, 45 mmol, 15 eq.) in dry tetrahydrofuran (THF) (30 mL) at −78° C. The temperature of the medium is allowed to return to room temperature and then the reaction is heated under reflux with stirring. After 1 hour, the solution is cooled to −78° C. and diluted with dichloromethane, and then water (10 mL) is slowly poured in. The solid obtained is filtered and washed with dichloromethane. The mother liquors are washed with water and with brine and then dried and concentrated to give 1.05 g (2.88 mmol) of a pasty compound (yield: 97%).

Synthesis of 4-[bis(4-formylphenyl)amino]-2-methoxybenzaldehyde or compound 9

MnO$_2$ (40 mg, 444 µmol) is added to a solution of compound 8 (27 mg, 74 µmol) in dichloromethane (2 ml). The suspension obtained is stirred for 48 hours at room temperature and then it is filtered. The solid obtained is washed with dichloromethane. The mother liquors are then concentrated to give 25 mg of compound 9 in the form of a yellow solid (yield: 91%).

Synthesis of 4-[bis(4-formylphenyl)amino]-2-hydroxybenzaldehyde or compound 10

A solution of compound 9 (310 mg, 860 µmol) in dichloromethane (5 mL) is added dropwise to a suspension of aluminium chloride (AlCl$_3$, 575 mg, 4.31 mmol, 5 eq.) in dichloromethane (10 mL) at −10° C. The mixture is stirred under reflux for 24 hours. It is then poured into a mixture of water and ice, and it is then vigorously stirred for 10 minutes. It is extracted with dichloromethane. The organic phase is washed with water and with brine, dried and concentrated to give a solid which is triturated in hexane to give 260 mg (754 µmol) of compound 10 in the form of a yellow powder (yield: 87%).

Synthesis of ethyl 4-{5-[bis(4-formylphenyl)amino]-2-formylphenoxy}butanoate or compound 11

K$_2$CO$_3$ (1.1 g, 8.0 mmol, 10 eq.) is added to a solution of compound 10 (280 mg, 810 µmol) in dry DMF (12 mL). The reaction is stirred for 15 minutes and ethyl bromobutanoate (175 µL, 1.22 mmol, 1.5 eq.) is slowly added. The mixture is stirred for 24 hours at room temperature and then concentrated. The residue is taken up in dichloromethane and water. The two-phase mixture is allowed to separate by settling, and the organic phase is washed several times with water. After drying and concentrating, a solid is obtained which is purified by chromatography (elution with a methanol gradient from 0 to 1% in dichloromethane) to give 275 mg (530 µmol) of compound 11 in the form of an orange powder (yield: 75%).

Synthesis of Compound 12

Compound 11 (160 mg, 348 µmol) in solution in THF (12 mL) is added dropwise to a suspension of sodium hydride (60% dispersion, 51 mg, 1.26 mmol, 3.60 eq.) and diethyl (2-methylbenzothiazole)phosphonate (328 mg, 1.15 mmol, 3.3 eq.) in dry THF (10 mL). The mixture is stirred at room temperature for 3 days, and then it is diluted with dichloromethane, washed with water and with brine. The organic phase is dried and concentrated. The residue obtained is triturated in pentane to give 220 mg (257 µmol) of compound 12 (yield: 74%).

$^1$H NMR (CDCl$_3$, 300 MHz) δ: 1.27 (t, 6.9, 3H); 2.24 (quint, 6.9 Hz, 2H); 2.60 (t, 6.9 Hz, 2H); 4.00 (t, 6.9 Hz, 2H); 4.19 (q, 6.9 Hz, 2H); 6.72 (d, 1.8 Hz, 1H); 6.79 (dd, 1.8 Hz, 8.4 Hz, 1H); 7.22 (d, 8.4 Hz, 4H); 7.33-7.65 (mult, 16H); 7.83 (d, 16.2 Hz, 1H); 7.89 (mult, 3H); 8.01 (d, 8.4 Hz, 1H); 8.03 (d, 8.4 Hz, 2H).

¹³C NMR (CDCl₃, 75 MHz) δ: 14.2; 24.5; 30.8; 60.6; 67.5; 108.0; 117.1; 120.3; 121.0; 121.4; 121.5; 122.5; 122.7; 122.8; 124.6; 125.1; 125.3; 126.2; 126.3; 128.7; 130.8; 132.4; 134.3; 136.8; 147.6; 148.8; 154.0; 154.1; 157.8; 167.1; 168.2; 173.0.

Figure 13:
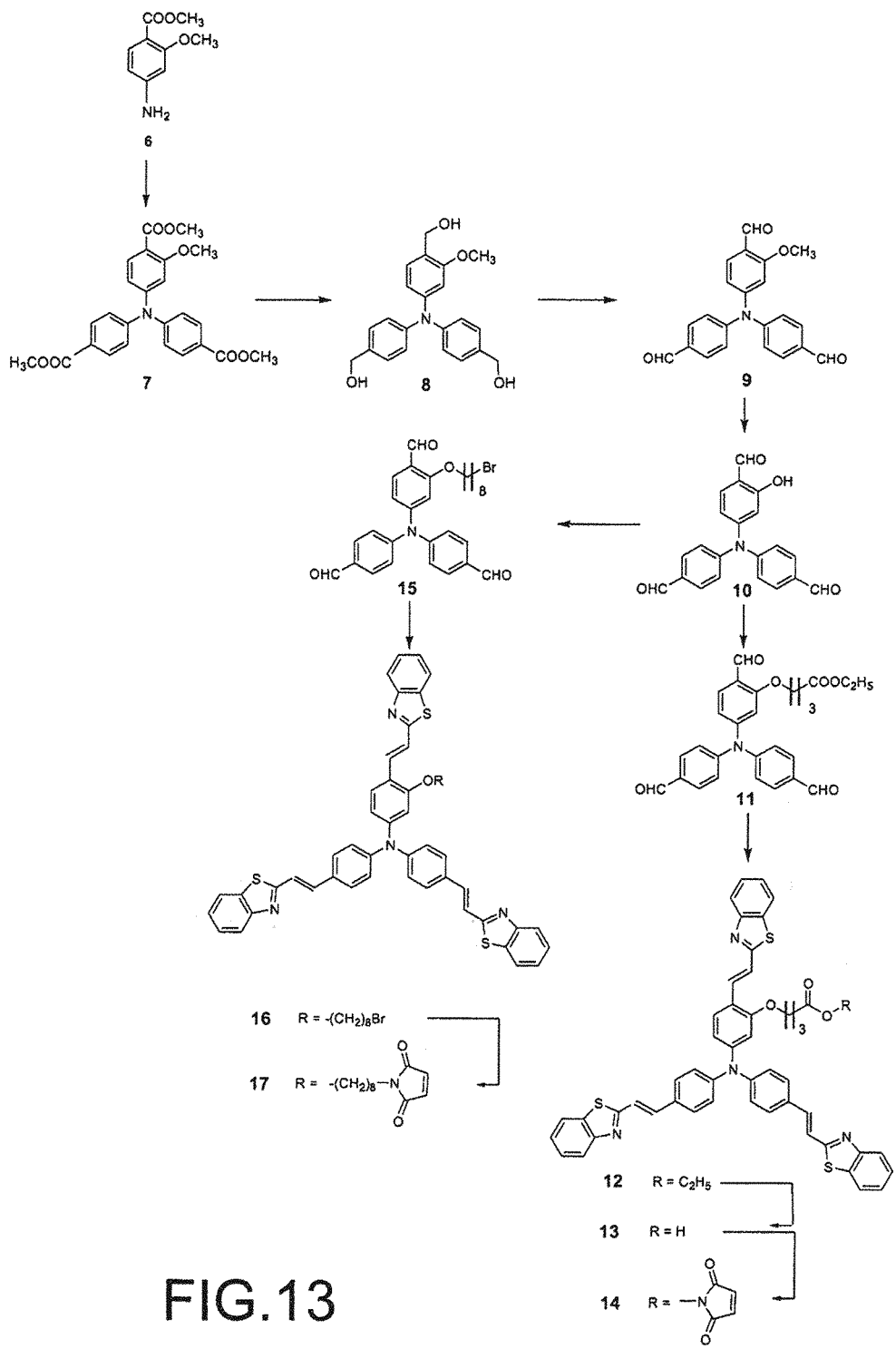
FIGS. 13 to 15 illustrate the schemes for the synthesis of other compounds according to the invention.

3.2. 4-{5-[Bis(4-[(E)-2-(1,3-benzothiazol-2-yl)vinyl]phenyl)amino]-2-[(E)-2-(1,3-benzothiazol-2-yl)vinyl]phenoxy}butanoic acid As visible in FIG. 13, the title compound or compound 13, which corresponds to the compound of general formula (I) in which $R_4$=spacer group —O(CH$_2$)$_3$COOH, $R_1$=$R_2$=$R_3$=group of formula (III-6), may be synthesized from compound 12 as obtained at point 3.1. above.

To do this, compound 12 (60 mg, 0.070 mmol) is dissolved in THF (2 mL). 2 mL of a saturated aqueous LiOH solution are added thereto, and the two-phase mixture obtained is vigorously stirred for 24 hours. Next, the mixture is acidified to pH 2 and diluted with dichloromethane. After allowing the mixture to separate by settling, the organic phase is separated, washed with water and then with brine, dried and concentrated to give a residue which is triturated in ether and pentane. 53 mg (63 μmol) of compound 13 are thus obtained (yield: 90%).

¹H NMR (CDCl₃, 300 MHz) δ: 2.32 (br, 2H); 2.59 (br, 2H); 4.01 (t, 6.0 Hz, 2H); 6.67 (d, 1.8 Hz, 1H); 6.75 (dd, 1.8 Hz, 8.4 Hz, 1H); 7.21 (d, 8.4 Hz, 4H); 7.30-7.65 (mult, 16H); 7.86-7.91 (mult, 3H); 8.01-8.04 (mult, 3H); 8.14 (d, 15.0 Hz, 1H).

¹³C NMR (CDCl₃, 75 MHz) δ: 25.0; 32.0; 68.6; 107.5; 116.9; 119.4; 120.1; 121.0; 121.5; 122.2; 122.8; 124.6; 125.0; 125.2; 126.5; 128.5; 128.7; 130.9; 132.8; 134.1; 134.3; 137.0; 147.5; 149.0; 153.1; 153.9; 158.1; 167.2; 168.7.

3.3. Succinimidyl 4-{5-[bis(4-[(E)-2-(1,3-benzothiazol-2-yl)vinyl]phenyl)amino]-2-[(E)-2-(1,3-benzothiazol-2-yl)vinyl]phenoxy}butanoate As visible in FIG. 13, the title compound or compound 14, which corresponds to the compound of general formula (I) in which $R_4$=spacer group —O(CH$_2$)$_3$C(O)O-succinimidyl, $R_1$=$R_2$=$R_3$=group of formula (III-6), may be synthesized from compound 13 as obtained at point 3.2. above.

To do this, compound 13 (40 mg, 50 μmol), N-hydroxysuccinimide (9 mg, 78 μmol) and DCC (11 mg) are dissolved in dichloromethane (1 mL) and the mixture is stirred for 24 hours. Next, the medium is evaporated, and taken up in a minimum of dichloromethane. The milky suspension is filtered, and the operation is repeated several times. The mother liquors are evaporated to dryness to give compound 14 in the form of an orange yellow powder.

¹H NMR (CDCl₃, 300 MHz) δ: 2.34 (quint, 6.3 Hz, 2H); 2.83 (s, 4H); 2.93 (t, 6.3 Hz, 2H); 4.06 (t, 6.0 Hz, 2H); 6.73 (d, 1.8 Hz, 1H); 6.80 (dd, 1.8 Hz, 8.4 Hz, 1H); 7.22 (d, 8.4 Hz, 4H); 7.35-7.65 (mult, 16H); 7.83 (d, 16.5 Hz, 1H); 7.90 (mult, 3H); 8.00 (d, 8.4 Hz, 2H); 8.02 (d, 8.4 Hz, 1H).

¹³C NMR (CDCl₃, 75 MHz) δ: 22.7; 25.6 (3C); 66.8; 108.0; 117.3; 120.2; 121.0; 121.4; 121.5; 122.7; 122.8; 124.6; 125.1; 125.3; 126.2; 126.4; 128.5; 128.7; 130.8; 132.3; 134.3; 138.9; 147.6; 148.8; 153.9; 154.0; 157.4; 167.2; 168.2; 168.3; 169.0.

3.4. (3-(8-Bromooctyloxy)-{4-[(E)-2-(benzo-thiazol-2-yl)vinyl]}-N,N-bis-{4-[(E)-2-(benzothiazol-2-yl)vinyl]phenyl}aniline As visible in FIG. 13, the title compound or compound 16, which corresponds to the compound of general formula (I) in which $R_4$=spacer group —O(CH$_2$)$_8$Br, $R_1$=$R_2$=$R_3$=group of formula (III-6), may be synthesized from compound 10 as obtained at point 3.1. above.

Synthesis of 2-(8-bromooctyloxy), 4-[N,N-bis(4-formyl-phenyl)]aminobenzaldehyde or compound 15

Compound 10 (100 mg, 290 μmol), 1,8-dibromooctane (800 μL, 1.18 g, 4.34 mmol, 15 eq.) and potassium carbonate (100 mg, 723 μmol, 2.5 eq.) are dissolved in dry acetone (10 mL). The white suspension is stirred at 45° C. for 24 hours. Next, ether is added and the mixture is filtered and washed with ether. After combining and concentrating the mother liquors, the residue is purified by column chromatography (elution: dichloromethane/n-hexane 1/1 to 4/1, v/v, and then dichloromethane and dichloromethane/methanol 99.5/0.5, v/v). Compound 15 is obtained in the form of a yellow solid (yield: 84%).

Synthesis of Compound 16

Diethyl(2-methylbenzothiazole)phosphonate (186 mg, 652 μmol, 3.5 eq.) is dissolved in dry THF (5 mL). Sodium hydride (60% dispersion, 25 mg, 625 μmol, 3.3 eq.) is added. After about 15 minutes, compound 15 (100 mg, 186 μmol) in solution in dry THF (5 mL) is added dropwise. After stirring for 24 hours at room temperature, the medium is evaporated to dryness and the residue purified by chromatography (elution with a gradient of methanol from 0 to 0.5% in dichloromethane) to give, after evaporation, 98 mg (106 μmol) of compound 16 in the form of an orange powder (yield: 57%).

¹H NMR (CDCl₃, 300 MHz) δ: 1.30-1.60 (br, 8H); 1.88 (br, 4H); 3.41 (t, 6.9 Hz, 2H); 3.94 (t, 6.3 Hz, 2H); 6.72 (br, 1H); 6.77 (d, 8.4 Hz, 1H); 7.22 (d, 8.4 Hz, 4H); 7.35-7.58 (mult, 16H); 7.84 (d, 16.5 Hz, 1H); 7.90 (mult, 3H); 8.01 (d, 7.6 Hz, 1H); 8.03 (d, 7.6 Hz, 2H).

¹³C NMR (CDCl₃, 75 MHz) δ: 26.1; 28.1; 28.7; 29.0; 29.2; 32.8; 33.9; 68.6; 108.1; 116.9; 120.3; 121.0; 121.4; 121.5; 122.8; 122.9; 124.6; 125.1; 125.3; 126.2; 126.4; 128.6; 129.0; 130.8; 132.8; 134.3; 134.4; 138.8; 147.7; 148.8; 154.0; 154.1; 158.2; 167.1; 168.3.

3.5. (3-(8-(2,5-Dioxo-1-aza)cyclopent-3-enyl)-octyloxy)-{4-[(E)-2-(benzothiazol-2-yl)vinyl]}-N,N-bis-{4-[(E)-2-(benzothiazol-2-yl)vinyl]phenyl}aniline As visible in FIG. 13, the title compound or compound 17, which corresponds to the compound of general formula (I) in which $R_4$=linking group —(CH$_2$)$_8$-succinimidyl, $R_1$=$R_2$=$R_3$=group of formula (III-6), may be synthesized from compound 16 as obtained at point 3.4. above.

Compound 16 (24 mg, 25.8 μmol), rac-7-oxabicyclo-[2.2.1]-heptene-2,3-dicarboxylic imide (5 mg, 28.4 μmol, 1.1 eq.) and K₂CO₃ (18 mg, 129 μmol, 5 eq.) are dissolved in 50 μL of dry DMF. The white suspension obtained is stirred at 55° C. for 24 hours. The progress of the reaction is monitored by TLC. Once the disappearance of the starting material is observed, the mixture is diluted with dichloromethane and washed several times with water. The organic phase is dried and concentrated. The residue is redissolved with 5 mL of anisole and heated under reflux for 2 hours. Next, the anisole is driven off under vacuum and the residue is purified by preparative TLC. 11 mg (12 μmol) of compound 17 are thus obtained in the form of an orange powder (yield: 47%).

¹H NMR (CDCl₃, 300 MHz) δ: 1.30-1.60 (br, 10H); 1.85 (quint, 2H); 3.52 (t, 7.2 Hz, 2H); 3.93 (t, 6.3 Hz, 2H); 6.67 (s, 4H); 6.72 (d, 1.8 Hz, 1H); 6.77 (dd, 1.8 Hz, 8.4 Hz, 1H); 7.22 (d, 8.4 Hz, 4H); 7.33-7.60 (mult, 16H); 7.84 (d, 16.2 Hz, 1H); 7.90 (mult, 3H); 8.01 (d, 7.6 Hz, 1H); 8.03 (d, 7.6 Hz, 2H).

$^{13}$C NMR (CDCl$_3$, 75 MHz) δ: 26.1; 26.6; 28.5; 29.0; 29.1; 29.2; 37.9; 68.6; 108.0; 116.9; 120.4; 121.0; 121.4; 121.5; 122.7; 122.9; 124.4; 125.0; 125.2; 126.3; 126.4; 128.7; 128.9; 130.6; 132.7; 134.0; 134.4 (2C); 136.8; 147.6; 148.9; 153.9; 154.0; 158.1; 167.3; 168.6; 171.0.

3.6. (3-(9-Bromononyloxy)-4-{4-[(E)-2-(pyridin-4-yl)vinyl]phenyl}-N,N-bis-{4-[(E)-2-(pyridin-4-yl)-vinyl]-phenyl}aniline The title compound or compound 22, which corresponds to the compound of general formula (I) in which R$_4$=linking group —O(CH$_2$)$_9$Br, R$_1$=R$_2$=R$_3$=group of formula (III-5), is synthesized from 3-methoxytriphenylamine or compound 18, which is commercially available, according to the scheme shown in FIG. 14.

Synthesis of 3-(N,N-diphenylamino)phenyl acetate or compound 19

A molar solution of BBr$_3$ (5.5 mL, 5.5 mmol, 1.5 eq.) is added dropwise over 45 minutes to a solution of compound 18 (1.012 g, 3.67 mmol) in dry dichloromethane (10 mL) cooled to −78° C. The resulting amber-coloured suspension is stirred for 1 hour at room temperature. The reaction medium is evaporated, redissolved in a pyridine/acetic anhydride mixture (6/4.5, v/v) and heated under reflux for 1 hour. After cooling to room temperature, the mixture is diluted with dichloromethane and washed with 10 mM hydrochloric acid until acidification of the aqueous phase is obtained, 2% Na$_2$CO$_3$ (m/v) and water. The organic phase is dried over Na$_2$SO$_4$, reduced to 5 mL and filtered on a small amount of silica. After drying, 1.046 g (3.45 mmol) of compound 19 are obtained in the form of a colourless oil (yield: 94%).

Synthesis of 2-iodo-5-(N,N-bis-(4-iodophenyl)amino)phenyl acetate or compound 20

Iodine (449 mg, 1.77 mmol, 7 eq.) is added to a solution of compound 19 (77 mg, 254 µmol) in dichloromethane, followed by red mercury oxide (384 mg, 1.77 mmol, 7 eq.), and the suspension obtained is stirred at room temperature for 3 days. Next, the suspension is filtered on Celite and the mother liquors washed with an Na$_2$S$_2$O$_3$ solution and water. The mother liquors are filtered a second time on silica and then evaporated to dryness to give 153 mg of compound 20 in the form of a white powder (yield: 88%).

Synthesis of 3-hydroxy-4-{4-[(E)-2-(pyridin-4-yl)vinyl]phenyl}-N,N-bis-{4-[(E)-2-(pyridin-4-yl)vinyl]-phenyl}aniline or compound 21

Palladium acetate (5 mg, 22 µmol) and tris-o-tolylphosphine (20 mg, 66 µmol) are dissolved in 3 mL of a dry TEA/DMF mixture (2/1, v/v). After stirring for 10 minutes 4-vinylpyridine (150 µL, 1.39 mmol, 5 eq.) and compound 20 (278 µmol, 1 eq.) are added and the mixture is heated for 3 hours at 85° C. under an inert atmosphere. Next, the medium is evaporated to dryness, and the red oil obtained is washed with pentane and then with ether. The residual red pasty residue is purified on a silica column (elution with a dichloromethane to dichloromethane/methanol gradient 97/3, v/v) to give an ochre powder corresponding to compound 21 (yield: 61%).

Synthesis of Compound 22

Compound 21 (103 mg, 1 eq.), 1,9-dibromononane (730 µL, 20 eq.) and potassium carbonate (125 mg, 5 eq.) are stirred for 3 hours at room temperature in DMF (1 mL). Next, the crude reaction product is poured into a large volume of ether (100 mL) and filtered on silica. The silica is thoroughly washed with ether. Next, it is washed with a dichloromethane/methanol mixture (95/5, v/v) and the mother liquors are concentrated and purified on a silica column (elution with a dichloromethane to dichloromethane/methanol gradient 97/3, v/v) to give, after evaporation, about 30 mg of compound 22 in the form of a red powder.

Figure 14:
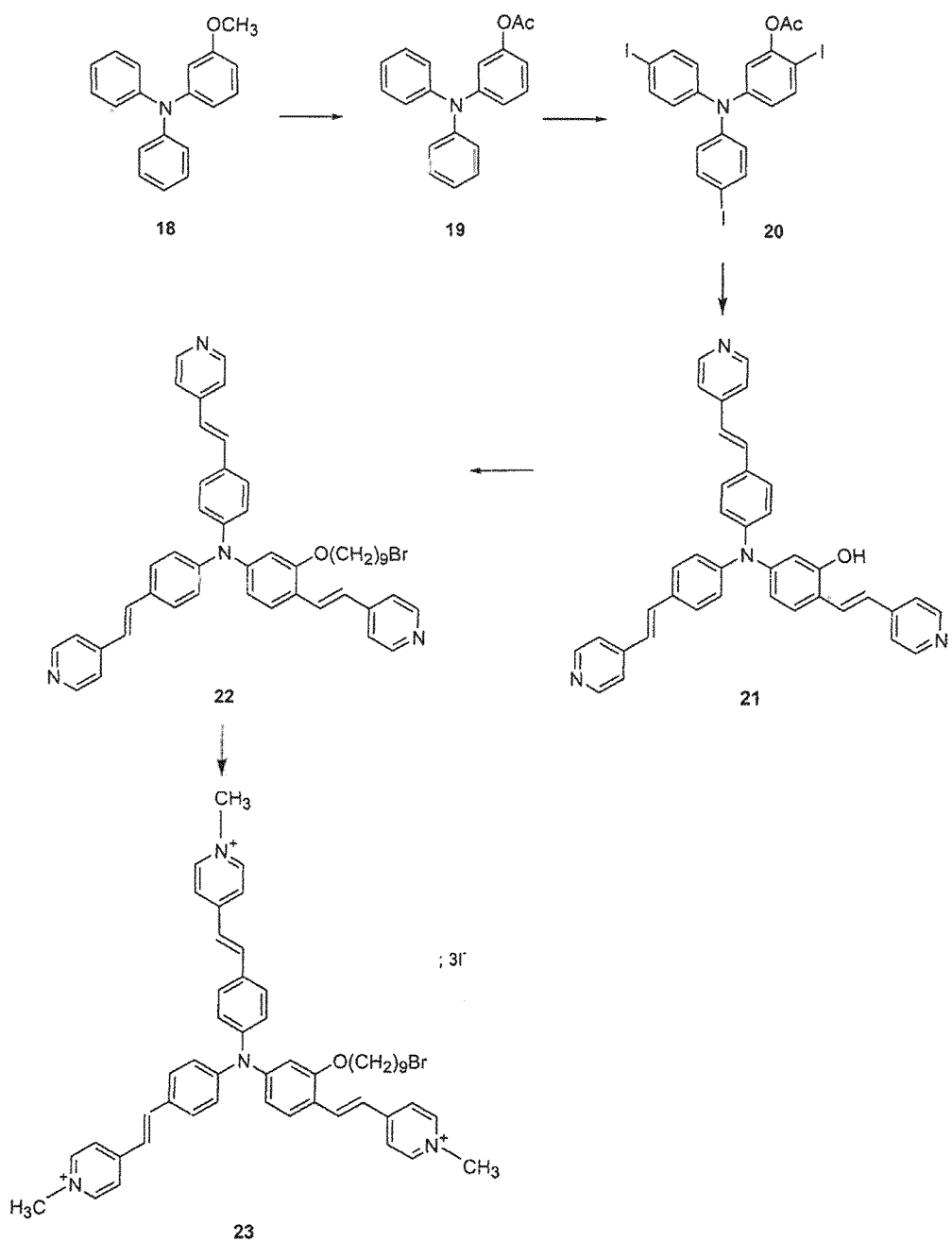

3.7. 3-(9-Bromononyloxy)-4,4',4''-tris(2-((E)-pyridin-4-yl)vinyl)triphenylamine tris-methiodide As visible in FIG. 14, the title compound or compound 23, which corresponds to the general formula (I) in which R$_4$=linking group —O(CH$_2$)$_9$Br, R$_1$=R$_2$=R$_3$=group of formula (II-5) in which R$_5$ is —CH$_3$, may be synthesized from compound 22 as obtained at point 3.6. above.

To do this, compound 22 (30 mg) is dissolved in 5 mL of a methanol/iodomethane mixture (1/1, v/v) and the whole is heated under reflux for 18 hours. The crude product is then evaporated and taken up in a minimum of methanol. A large quantity of ether is added. The resulting precipitate is filtered and washed with ether and then with pentane to give compound 23 in the form of a red powder (yield: 82%).

3.8. Methyl 4-(N,N-bis-(4-(2-(pyridin-4-yl)vinyl))phenyl)aminobenzoate

Figure 15:
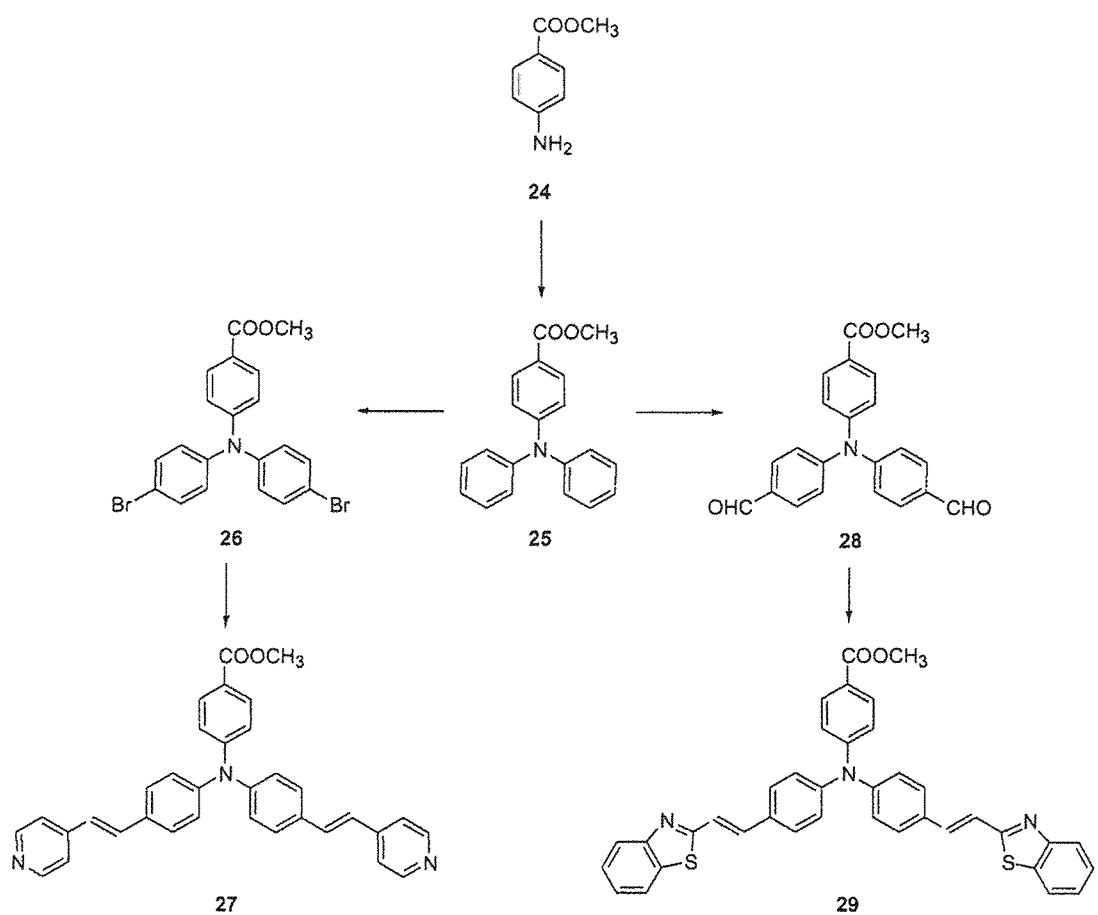

The title compound or compound 27, which corresponds to the compound of general formula (I) in which R$_4$=H, R$_1$=spacer group —COOCH$_3$, R$_2$=R$_3$=group of formula (III-5), is synthesized from methyl 4-aminobenzoate or compound 24, which is commercially available, according to the scheme shown in FIG. 15.

Synthesis of methyl 4-(N,N-diphenylamino)benzoate or compound 25

Caesium carbonate (1.6 g, 4.91 mmol), palladium acetate (50 mg, 0.22 mmol), tris-tert-butylphosphine (300 µL, at 10% in hexane, 0.15 mmol) and bromobenzene (440 µL, 657.4 mg, 4.91 mmol) are added under nitrogen to a solution of compound 24 (500 mg, 3.31 mmol) in dry toluene (20 mL). The reaction medium is heated under reflux for 18 hours, then the same quantities of reagents (caesium carbonate, palladium and phosphine) are again added and the mixture is again heated for 18 hours. At the end of the reaction, the crude product is filtered on Celite and diluted with ethyl acetate. The mother liquors are washed with brine and then with water and finally dried over sodium sulphate. The residue obtained is purified on a silica gel column (elution with an n-hexane/AcOEt mixture 85/15, v/v). Compound 25 is thus obtained in the form of a yellow oil which crystallizes after cooling to −4° C. (yield: 91%).

Synthesis of methyl 4-(N,N-bis-(4-bromophenyl)amino)benzoate or compound 26

N-Bromosuccinimide (708 mg, 3.98 mmol) is added to a solution of compound 25 (550 mg, 1.81 mmol) in chloroform.

The reaction is heated for 2 hours and then cooled to room temperature. The crude reaction product is then washed with water and then with brine and dried over magnesium sulphate. The residue obtained is purified on a silica gel column (elution with an n-hexane/AcOEt mixture 85/15, v/v). Compound 26 is isolated in the form of a yellow powder (yield: 98%).

Synthesis of Compound 27

4-Vinylpyridine (94.6 mg, 0.90 mmol), palladium acetate (10 mg, 0.04 mmol) and tris-o-tolylphosphine (40.7 mg, 0.13 mmol) are added under nitrogen to a solution of compound 26 (138 mg, 0.30 mmol) in 15 mL of a dry and degassed TEA/DMF mixture (2/1). The reaction medium is heated under reflux for 18 hours. At the end of the reaction, the crude product is filtered on Celite and diluted with ethyl acetate. The mother liquors are washed with brine and then with water and finally dried over sodium sulphate. The residue obtained is purified on a silica gel column (elution with a dichloromethane/methanol mixture 95/5, v/v). Compound 27 is obtained in the form of an orange powder (yield: 59%).

3.9. Methyl 4-(N,N-bis-(4-(2-(benzothiazol-2-yl)vinyl))phenyl)aminobenzoate

As visible in FIG. 15, the title compound or compound 29, which corresponds to the compound of general formula (I) in which $R_4$=H, $R_1$=spacer group —COOCH$_3$, $R_2$=$R_3$=group of formula (III-6), may be synthesized from compound 25 as obtained at point 3.7. above.

Synthesis of methyl 4-(N,N-bis-(4-formylphenyl)amino)benzoate or compound 28

DMF (2.9 mL, 37.5 mmol) is cooled to 0° C. and phosphoryl trichloride (POCl$_3$, 3.7 mL, 40 mmol) is added dropwise under a nitrogen atmosphere. The mixture is stirred for 1 hour at 0° C. Compound 25 (500 mg, 1.6 mmol) is slowly added to this mixture and the mixture is vigorously stirred at 95° C. for 4 hours. After cooling, the reaction mixture is poured into ice and neutralized by adding concentrated sodium hydroxide. The mixture obtained is extracted several times with dichloromethane. The organic phase is washed with brine and then with water and finally dried over sodium sulphate. The residue obtained is purified on a silica gel column (elution with an n-hexane/AcOEt mixture 75/25). Compound 28 is obtained in the form of an orange powder (yield: 35%).

Synthesis of Compound 29

Diethyl [(benzothiazol-2-yl)methyl]phosphonate (as described in J. Am. Chem. Soc. 1993, 115, 7192-7198 [9]; 175 mg, 0.61 mmol), NaH (50 mg, 1.25 mmol, dispersion at 60%) and a drop of crown ether 18-C-6 are dissolved in dry THF (10 mL). The resulting red solution is cooled to 0° C. and a solution of compound 28 (100 mg, 0.28 mmol) in dry THF (5 mL) is added dropwise. The mixture is stirred for 24 hours at room temperature. Next, the reaction is stopped by adding water (2 mL) and diluted with dichloromethane. The organic phases are washed with brine and then with water and finally dried over sodium sulphate. The residue obtained is purified on a silica gel column (elution with an AcOEt/AcOH mixture, 99/1). Compound 29 is obtained in the form of a yellow powder (yield: 41%).

Example 4

Functionalization of Oligonucleotides 4.1. Functionalization with Compound 16:

An oligonucleotide having a terminal functional group, at position 3' or 5', of the thiophosphate type and containing counter-ions of the ammonium ($NH_4^+$) type is dissolved in a solution of crown ether 18-C-6 in methanol (treated beforehand with a chelating resin) in an amount of about 20 OD per mL. Compound 16 (about 2 mg) is added, and the mixture is vortexed and then stirred at 35° C. for 6 hours.

The mixture is then subjected to a purification procedure according to the procedure below: the mixture is first of all evaporated, taken up in water (1 mL) and extracted several times with dichloromethane and then with ethyl acetate until the organic phases remain colourless. The residual nonaqueous solvent is expelled under vacuum, and the aqueous solution is diluted with 1M NaCl in one mL of a water/acetonitrile mixture 5/1 (v/v). This solution is purified on a steric exclusion column (exclusion<1000 Da) and the first coloured eluting fraction is recovered. If necessary, the fraction obtained is purified by HPLC according to the usual procedures. Conventionally, the purification is performed using a column of reversed phase type (RP-18) and a water/acetonitrile or water/methanol elution system, with a pH close to 7 and comprising a dissolved salt (about 0.1M) of the (trialkyl)ammonium acetate type. The isolated fractions are freeze-dried a minimum of three times.

4.2. Functionalization with Compound 14:

An oligonucleotide comprising a primary amine functional group is dissolved in a 0.5% NaHCO$_3$ buffer at pH 9.5 in an amount of 10 OD per 500 µL. Compound 14 (about 1 to 2 mg) in solution in DMF (about 300 µL, purified beforehand from the amino impurities) is added. The mixture is stirred for 24 hours at 35° C.

The mixture is then subjected to a purification procedure identical to that described at point 4.1. above.

The invention claimed is:

1. A compound corresponding to the general formula (I) below:

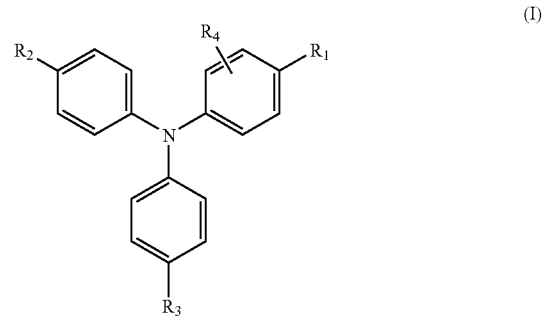

(I)

in which:

$R_4$ represents a hydrogen atom;

$R_1$ and $R_2$ represent, independently of each other, a group of formula (II) below:

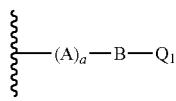

(II)

in which:

$Q_1$ represents:

a heterocyclic group of formula (i) below:

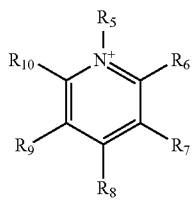

(i)

in which $R_5$ represents a hydrocarbon group; any one of $R_6$ to $R_{10}$ represents a covalent bond linking said heterocyclic group to B, while the others from $R_6$ to $R_{10}$ represent, independently of each other, a hydrogen atom or a hydrocarbon group; or a heterocyclic group of formula (ii) or (iii) below:

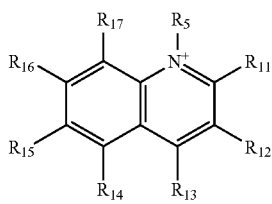

(ii)

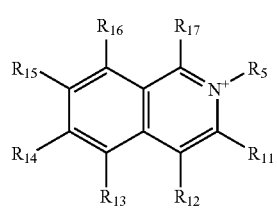

(iii)

in which $R_5$ represents a hydrocarbon group; any one of $R_{11}$ to $R_{17}$ represents a covalent bond linking said heterocyclic group to B, while the others from $R_{11}$ to $R_{17}$ represent, independently of each other, a hydrogen atom or a hydrocarbon group, it being possible for $R_{12}$, $R_{14}$ and $R_{16}$ to also form, respectively with $R_{11}$ and/or $R_{13}$, $R_{13}$ and/or $R_{15}$, and with $R_{15}$ and/or $R_{17}$, a bridging group; or a heterocyclic group of formula (iv) below:

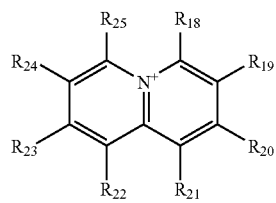

(iv)

in which any one of $R_{18}$ to $R_{25}$ represents a covalent bond linking said heterocyclic group to B, while the others from $R_{18}$ to $R_{25}$ represent, independently of each other, a hydrogen atom or a hydrocarbon group, it being possible for $R_{19}$, $R_{21}$, $R_{23}$ and $R_{25}$ to also form, respectively with $R_{18}$ and/or $R_{20}$, $R_{20}$ and/or $R_{22}$, $R_{22}$ and/or $R_{24}$, and with $R_{24}$ and/or $R_{18}$, a bridging group;

a heterocyclic group of formula (v) below:

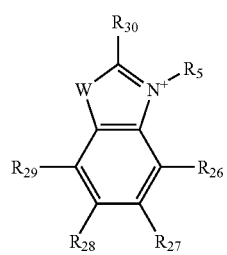

(v)

in which $R_5$ represents a hydrocarbon group; W represents an oxygen atom or a group $—N(R_{31})—$ in which $R_{31}$ is a hydrogen atom or a hydrocarbon group, or a group $—C(R_{31})(R_{32})—$ in which $R_{31}$ and $R_{32}$ are, independently of each other, a hydrogen atom or a hydrocarbon group; $R_{30}$ represents a covalent bond linking said heterocyclic group to B, while $R_{26}$ to $R_{29}$ represent, independently of each other, a hydrogen atom or a hydrocarbon group, it being possible for $R_{27}$ to also form with $R_{26}$ and/or $R_{28}$ a bridging group, it being possible for $R_{28}$ itself to form with $R_{29}$ a bridging group;

a is equal to 0 (in which case A is absent) or 1 (in which case A is present);

A and B represent the groups below:

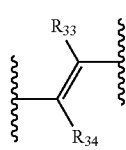

(A)

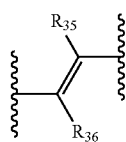

(B)

in which $R_{33}$ to $R_{36}$ represent, independently of each other, a hydrogen atom or a hydrocarbon group, it being possible for $R_{33}$ and $R_{36}$ to each also form with $R_{34}$ and/or $R_{35}$ a bridging group;

$R_3$ represents a hydrogen or halogen atom, a hydrocarbon group or a group of formula (II) as defined above;

in which each of the abovementioned hydrocarbon groups may be substituted with one or more substituents, which are identical or different, and comprise one or more heteroatoms;

said compound further comprising a number of anions wherein the sum of the negative charge of the anions is equal to the number of positively charged (i), (ii), (iii), (iv) and/or (v) groups within the compound.

2. The compound of claim 1, which corresponds to the general formula (I) in which $R_1$ and $R_2$ are identical, and $R_3$ represents a hydrogen or halogen atom, a hydrocarbon group or a group of formula (II) identical to $R_1$ and $R_2$.

3. The compound of claim 2, in which both $R_1$ and $R_2$ represent a group of formula (II) in which a is equal to 0, and both $R_{35}$ and $R_{36}$ of B represents a hydrogen atom or a $C_1$ to $C_4$ alkyl groups.

4. The compound of claim 3, in which both $R_1$ and $R_2$ represent a group of formula (II) in which $Q_1$ represents a group of formula (i) or a group of formula (v).

5. The compound of claim 4, in which both $R_1$ and $R_2$ represent a group chosen from:

(a) groups of formula (II-1) below:

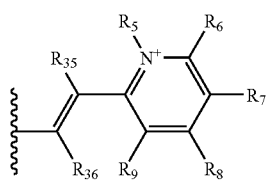

in which $R_5$ represents a $C_1$ to $C_4$ alkyl group, and $R_6$ to $R_9$, $R_{35}$ and $R_{36}$ represent, independently of each other, a hydrogen atom or a $C_1$ to $C_4$ alkyl group;

(b) groups of formula (II-2) below:

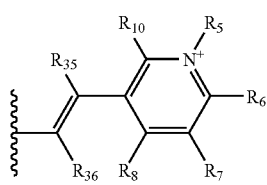

in which $R_5$ represents a $C_1$ to $C_4$ alkyl group, and $R_6$ to $R_8$, $R_{10}$, $R_{35}$ and $R_{36}$ represent, independently of each other, a hydrogen atom or a $C_1$ to $C_4$ alkyl group; and (c) groups of formula (II-3) below:

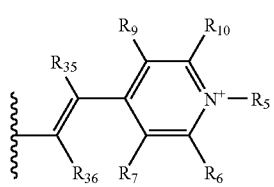

in which $R_5$ represents a $C_1$ to $C_4$ alkyl group, and $R_6$, $R_7$, $R_9$, $R_{10}$, $R_{35}$ and $R_{36}$ represent, independently of each other, a hydrogen atom or a $C_1$ to $C_4$ alkyl group.

6. The compound of claim 5, in which both $R_1$ and $R_2$ represent a group of formula (II-5) below:

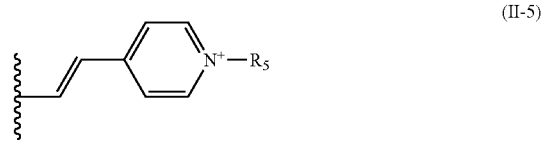

in which $R_5$ represents a $C_1$ to $C_4$ alkyl group.

7. The compound of claim 6, in which both $R_1$ and $R_2$ represent a group of formula (II-5) in which $R_5$ represents a methyl group, and $R_3$ represents a hydrogen atom or a group of formula (II-5) identical to $R_1$ and $R_2$.

8. The compound of claim 7, which is a bis[4-(2-N-methylpyridinium-4-ylvinyl)phenyl]phenylamine halide or a tris-[4-(2-N-methylpyridinium-4-ylvinyl)phenyl]amine halides.

9. A composition comprising at least one compound of general formula (I) as defined in claim 1, in solution in a solvent.

10. A biomolecule labelled with at least one compound of general formula (I) according to claim 1.

11. The biomolecule according to claim 10, which is a nucleic acid, a protein, a polypeptide or a fragment thereof.

12. The compound of claim 8, which is a bis[4-(2-N-methylpyridinium-4-ylvinyl)phenyl]phenylamine iodide or a tris-[4-(2-N-methylpyridinium-4-ylvinyl)phenyl]amine iodide.

13. A compound corresponding to the general formula (I) below:

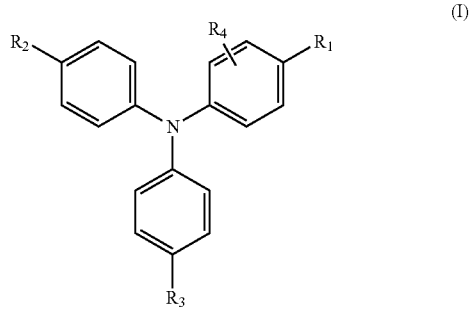

in which:

$R_4$ represents a hydrogen atom;

$R_1$ represents a linking group;

$R_2$ and $R_3$ represent, independently of each other, a group of formula (III) below:

in which:

$Q_2$ represents:

a heterocyclic group of formula (i) below:

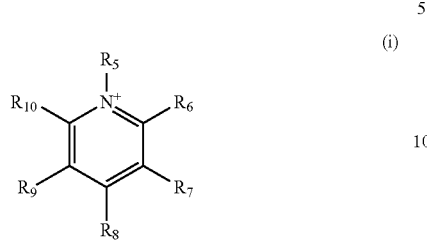

in which $R_5$ represents a hydrocarbon group; any one of $R_6$ to $R_{10}$ represents a covalent bond linking said heterocyclic group to B, and the others from $R_6$ to $R_{10}$ represent, independently of each other, a hydrogen atom or a hydrocarbon group; or a heterocyclic group of formula (ii) or (iii) below:

in which $R_5$ represents a hydrocarbon group; any one of $R_{11}$ to $R_{17}$ represents a covalent bond linking said heterocyclic group to B, and the others from $R_{11}$ to $R_{17}$ represent, independently of each other, a hydrogen atom or a hydrocarbon group, it being possible for $R_{12}$, $R_{14}$ and $R_{16}$ to also form, respectively with $R_{11}$ and/or $R_{13}$, $R_{13}$ and/or $R_{15}$, and with $R_{15}$ and/or $R_{17}$, a bridging group; or a heterocyclic group of formula (iv) below:

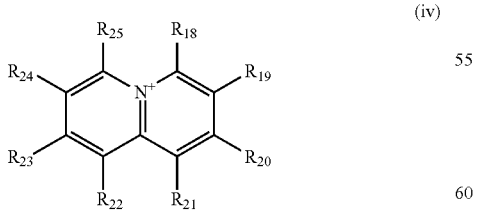

in which any one of $R_{18}$ to $R_{25}$ represents a covalent bond linking said heterocyclic group to B, and the others from $R_{18}$ to $R_{25}$ represent, independently of each other, a hydrogen atom or a hydrocarbon group, it being possible for $R_{19}$, $R_{21}$, $R_{23}$ and $R_{25}$ to also form, respectively with $R_{18}$ and/or $R_{20}$, $R_{20}$ and/or $R_{22}$, $R_{22}$ and/or $R_{24}$, and with $R_{24}$ and/or $R_{18}$, a bridging group; or a heterocyclic group of formula (v) below:

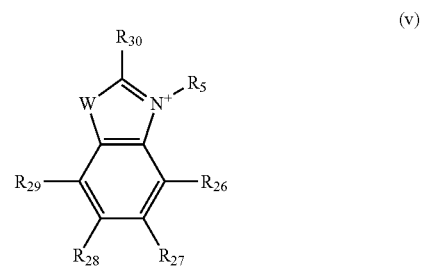

in which $R_5$ represents a hydrocarbon group; W represents an oxygen atom or a group —N($R_{31}$)— in which $R_{31}$ is a hydrogen atom or a hydrocarbon group, or a group —C($R_{31}$)($R_{32}$)— in which $R_{31}$ and $R_{32}$ are, independently of each other, a hydrogen atom or a hydrocarbon group; $R_{30}$ represents a covalent bond linking said heterocyclic group to B, while $R_{26}$ to $R_{29}$ represent, independently of each other, a hydrogen atom or a hydrocarbon group, it being possible for $R_{27}$ to also form with $R_{26}$ and/or $R_{28}$ a bridging group, it being possible for $R_{28}$ itself to form with $R_{29}$ a bridging group;

a heterocyclic group of formula (vi) below:

in which $R_6$ to $R_{10}$ are as defined in formula (i);

a heterocyclic group of formula (vii) or (viii) below:

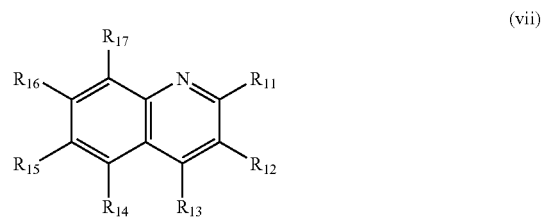

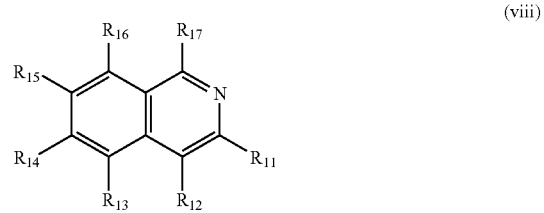

in which $R_{11}$ to $R_{17}$ are as defined in formulae (ii) and (iii) above; or a heterocyclic group of formula (ix) below:

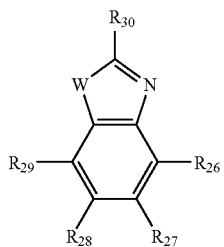

(ix)

in which W, $R_{26}$ to $R_{30}$ are as defined in formula (v);

a is equal to 0 (in which case A is absent) or 1 (in which case A is present);

A and B represent the groups below:

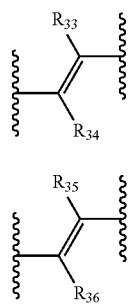

in which $R_{33}$ to $R_{36}$ represent, independently of each other, a hydrogen atom or a hydrocarbon group, it being possible for $R_{33}$ and $R_{36}$ to each also form with $R_{34}$ and/or $R_{35}$ a bridging group;

in which the linking group is a functional group capable of allowing the grafting, by a chemical reaction, of the compound on a biomolecule, or a hydrocarbon group comprising such a functional group, and in which each of the abovementioned hydrocarbon groups may be substituted with one or more substituents, which are identical or different, and comprise one or more heteroatoms;

said compound further comprising a number of anions wherein the sum of the negative charge of the anions is equal to the number of positively charged (i), (ii), (iii), (iv) and/or (v) groups within the compound.

14. A composition comprising at least one compound of general formula (I) as defined in claim 13, in solution in a solvent.

15. The compound of claim 13, in which $R_2$ and $R_3$ are identical.

16. The compound of claim 15, in which both $R_2$ and $R_3$ represent a group of formula (III) in which a is equal to 0, both $R_{35}$ and $R_{36}$ of B represent a hydrogen atom or a $C_1$ to $C_4$ alkyl group.

17. The compound of claim 16, in which both $R_2$ and $R_3$ represent a group of formula (III) in which $Q_2$ represents a group of formula (vi) or a group of formula (iv).

18. The compound of claim 17, in which both $R_2$ and $R_3$ are chosen from:

(a) groups of formula (III-1) below:

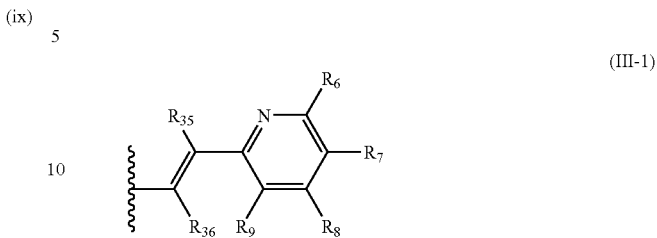

(III-1)

in which $R_6$ to $R_9$, $R_{35}$ and $R_{36}$ represent, independently of each other, a hydrogen atom or a $C_1$ to $C_4$ alkyl group;

(b) groups of formula (III-2) below:

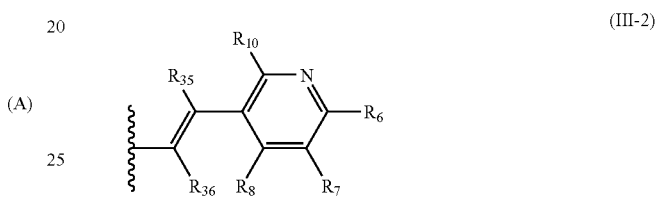

(III-2)

in which $R_6$ to $R_8$, $R_{10}$, $R_{35}$ and $R_{36}$ represent, independently of each other, a hydrogen atom or a $C_1$ to $C_4$ alkyl group; and (c) groups of formula (III-3) below:

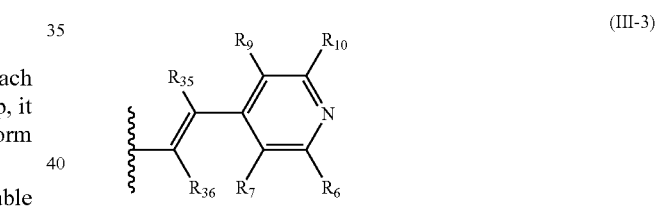

(III-3)

in which $R_6$, $R_7$, $R_9$, $R_{10}$, $R_{35}$ and $R_{36}$ represent, independently of each other, a hydrogen atom or a $C_1$ to $C_4$ alkyl group.

19. The compound according to claim 15, in which, when $R_4$ represents the linking group, then it is at the α position of the group $R_1$.

20. The compound according to claim 15, in which $R_4$ is a linking group, while $R_1$, $R_2$ and $R_3$ all represent a group of formula (III-5) or (III-6) below:

(III-5)

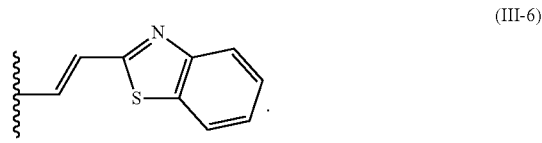

(III-6)

21. The compound according to claim 20, which is chosen from the following compounds:

- ethyl 4-{5-[bis(4-[(E)-2-(1,3-benzothiazol-2-yl)vinyl]phenyl)amino]-2-[(E)-2-(1,3-benzothiazol-2-yl)vinyl]phenoxy}butanoate;
- 4-{5-[bis(4-[(E)-2-(1,3-benzothiazol-2-yl)vinyl]phenyl)amino]-2-[(E)-2-(1,3-benzothiazol-2-yl)vinyl]phenoxy}butanoic acid;
- succinimidyl 4-{5-[bis(4-[(E)-2-(1,3-benzothiazol-2-yl)vinyl]phenyl)amino]-2-[(E)-2-(1,3-benzothiazol-2-yl)vinyl]phenoxy}butanoate;
- (3-(8-bromooctyloxy)-{4-[(E)-2-(benzothiazol-2-yl)vinyl]}-N,N-bis-{4-[(E)-2-(benzothiazol-2-yl)vinyl]phenyl}aniline;
- (3-(8-(2,5-dioxo-1-aza)cyclopent-3-enyl)octyloxy)-{4-[(E)-2-(benzothiazol-2-yl)vinyl]}-N,N-bis-{4-[(E)-2-(benzothiazol-2-yl)vinyl]phenyl}aniline;
- (3-(9-bromononyloxy)-4-{4-[(E)-2-(pyridin-4-yl)vinyl]phenyl}-N,N-bis-{4-[(E)-2-(pyridin-4-yl)vinyl]phenyl}aniline;
- 3-(9-bromononyloxy)-4,4'4''-tris(2-((E)-pyridin-4-yl)vinyl)triphenylamine tris-methiodide;
- methyl 4-(N,N-bis(4-(2-(pyridin-4-yl)vinyl))phenyl)aminobenzoate; and
- methyl 4-(N,N-bis(4-(2-(benzothiazol-2-yl)vinyl))phenyl)aminobenzoate.

* * * * *

UNITED STATES PATENT AND TRADEMARK OFFICE
CERTIFICATE OF CORRECTION

PATENT NO.       : 8,664,400 B2
APPLICATION NO.  : 12/514040
DATED            : March 4, 2014
INVENTOR(S)      : Allain et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 18 days.

Signed and Sealed this
Twenty-ninth Day of September, 2015

Michelle K. Lee
*Director of the United States Patent and Trademark Office*